(12) United States Patent
Sbianchi et al.

(10) Patent No.: US 9,988,056 B2
(45) Date of Patent: Jun. 5, 2018

(54) SYSTEMS AND METHODS FOR CONTROLLING SENSOR-BASED DATA ACQUISITION AND SIGNAL PROCESSING IN VEHICLES

(71) Applicants: Fabio Sbianchi, Rome (IT); Gianfranco Giannella, Rome (IT)

(72) Inventors: Fabio Sbianchi, Rome (IT); Gianfranco Giannella, Rome (IT)

(73) Assignee: Octo Telematics SPA, Rome (IT)

( * ) Notice: Subject to any disclaimer, the term of this patent is extended or adjusted under 35 U.S.C. 154(b) by 230 days.

(21) Appl. No.: 14/969,100

(22) Filed: Dec. 15, 2015

(65) Prior Publication Data

US 2017/0166217 A1    Jun. 15, 2017

(51) Int. Cl.

| | |
|---|---|
| *G05D 1/00* | (2006.01) |
| *G05D 3/00* | (2006.01) |
| *G06F 7/00* | (2006.01) |
| *G06F 17/00* | (2006.01) |
| *B60W 40/09* | (2012.01) |
| *A61B 5/18* | (2006.01) |
| *B60W 40/02* | (2006.01) |
| *B60W 40/105* | (2012.01) |
| *B60W 40/107* | (2012.01) |

(Continued)

(52) U.S. Cl.
CPC ............ *B60W 40/09* (2013.01); *A61B 5/18* (2013.01); *B60W 40/02* (2013.01); *B60W 40/105* (2013.01); *B60W 40/107* (2013.01); *B60W 40/109* (2013.01); *G06F 11/3089* (2013.01); *H04B 1/10* (2013.01); *H04L 67/12* (2013.01)

(58) Field of Classification Search
CPC .... B60W 40/09; B60W 40/02; B60W 40/105; B60W 40/107; B60W 40/109; A61B 5/18; B60R 21/32; G06F 7/00
USPC .............................................. 701/1; 280/735
See application file for complete search history.

(56) References Cited

U.S. PATENT DOCUMENTS

| | | | |
|---|---|---|---|
| 5,490,067 A | 2/1996 | Teguri et al. | |
| 5,904,368 A | * 5/1999 | Blackburn | G01S 15/52 280/735 |

(Continued)

OTHER PUBLICATIONS

PCT International Search Report dated Apr. 3, 2017 for PCT Application No. PCT/IB016/001879 filed on Dec. 12, 2016 to Octo Telematics S.P.A.

*Primary Examiner* — Mahmoud S Ismail
(74) *Attorney, Agent, or Firm* — Finnegan, Henderson, Farabow, Garrett & Dunner LLP

(57) ABSTRACT

Systems and methods are provided for dynamically controlling sensor-based data acquisition in vehicles. The disclosed embodiments may receive signals associated with sensors in a vehicle, wherein the signals are associated with sampling rates, and apply bandwidth filters to the signals to create filtered signals. The disclosed embodiments may also detect an occurrence of an event by comparing the filtered signals to one or more event thresholds and transmit event data to a control system when the event thresholds are exceeded. The disclosed embodiments also may dynamically adjust signals, sampling rates, bandwidth filters, a generated event score, and the event thresholds based on changes to a set of control variables. The control variables may depend on signals associated with a set of sensors in a vehicle or on boundary conditions and signals associated to an external system.

18 Claims, 8 Drawing Sheets

(51) Int. Cl.
  *B60W 40/109* (2012.01)
  *G06F 11/30* (2006.01)
  *H04B 1/10* (2006.01)
  *H04L 29/08* (2006.01)
  *B60R 21/16* (2006.01)

(56) References Cited

U.S. PATENT DOCUMENTS

| | | |
|---|---|---|
| 5,906,393 A | 5/1999 | Mazur et al. |
| 2013/0096731 A1* | 4/2013 | Tamari ................ G06F 11/3013 701/1 |
| 2015/0244431 A1* | 8/2015 | Vosburgh ................ H04B 7/04 375/347 |

* cited by examiner

SYSTEMS AND METHODS FOR CONTROLLING SENSOR-BASED DATA ACQUISITION AND SIGNAL PROCESSING IN VEHICLES

BACKGROUND

The present disclosure generally relates to systems and methods for dynamically controlling sensor-based data acquisition in vehicles. More particularly, and without limitation, the disclosed embodiments relate to systems and methods for dynamically adjusting signals and signal processing parameters based on continually fluctuating states of data.

Understanding the operation of a vehicle can require a great deal of information and processing power. This information may include data about the current state of the vehicle (e.g., its position, speed, acceleration, etc.), information about current road conditions (e.g., weather, traffic, road curvature, etc.), and information about the driver (e.g., the driver's driving history, mental state, etc.), among other things. Conventional data acquisition systems fail to provide efficient ways of collecting, processing, and using all of this information in a robust fashion. Therefore, such systems may be computationally inefficient or may sacrifice speed for accuracy.

SUMMARY

The disclosed embodiments include systems and methods for dynamically controlling sensor-based data acquisition in vehicles. The disclosed embodiments may continuously and dynamically adjust types of sensor signals collected, their respective sampling rates, and event detection algorithms to modify data acquisition in real-time or near real-time. The disclosed embodiments may adjust these parameters based on changes to control variables updating over time. In some aspects, these control variables may be based on information related to the vehicle, road, surroundings, driver, or other considerations.

The disclosed embodiments include, for example, a system for dynamically controlling sensor-based data acquisition in vehicles. The system may include a memory storing a set of instructions and one or more processors configured to execute the set instructions to perform one or more operations. The operations may include receiving a set of signals associated with a set of sensors in a vehicle, wherein the set of signals is associated with a set of sampling rates. The operations may also include applying a set of bandwidth filters to the set of signals to create a set of filtered signals. The operations may also include detecting an occurrence of an event by comparing an event score based on the set of filtered signals with an event threshold. The operations may also include outputting event data to a control center when the event score exceeds the event threshold, wherein at least one of the set of signals, the set of sampling rates, the set of bandwidth filters, the event score, or the event threshold is dynamically adjusted based on a change to a set of control variables.

The disclosed embodiments also include, for example, a method for dynamically controlling sensor-based data acquisition in vehicles, comprising the following operations performed via one or more processors associated with a device within the vehicle. The method may include receiving a set of signals associated with a set of sensors in a vehicle, wherein the set of signals is associated with a set of sampling rates. The method may also include applying a set of bandwidth filters to the set of signals to create a set of filtered signals. The method may also include detecting an occurrence of an event by comparing an event score based on the set of filtered signals with an event threshold. The method may also include outputting event data to a control center when the event score exceeds the event threshold, wherein at least one of the set of signals, the set of sampling rates, the set of bandwidth filters, the event score, or the event threshold is dynamically adjusted based on a change to a set of control variables.

The disclosed embodiments also include, for example, a tangible, non-transitory computer-readable medium (memory) storing instructions, that, when executed by at least one processor, cause the at least one processor to perform a method for dynamically controlling sensor-based data acquisition in vehicles. The method may include receiving a set of signals associated with a set of sensors in a vehicle, wherein the set of signals is associated with a set of sampling rates. The method may also include applying a set of bandwidth filters to the set of signals to create a set of filtered signals. The method may also include detecting an occurrence of an event by comparing an event score based on the set of filtered signals with an event threshold. The method may also include outputting event data to a control center when the event score exceeds the event threshold, wherein at least one of the set of signals, the set of sampling rates, the set of bandwidth filters, the event score, or the event threshold is dynamically adjusted based on a change to a set of control variables.

Additional features and advantages of the disclosed embodiments will be set forth in part in the description that follows, and in part will be obvious from the description, or may be learned by practice of the disclosed embodiments. The features and advantages of the disclosed embodiments will be realized and attained by means of the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Figure 1:
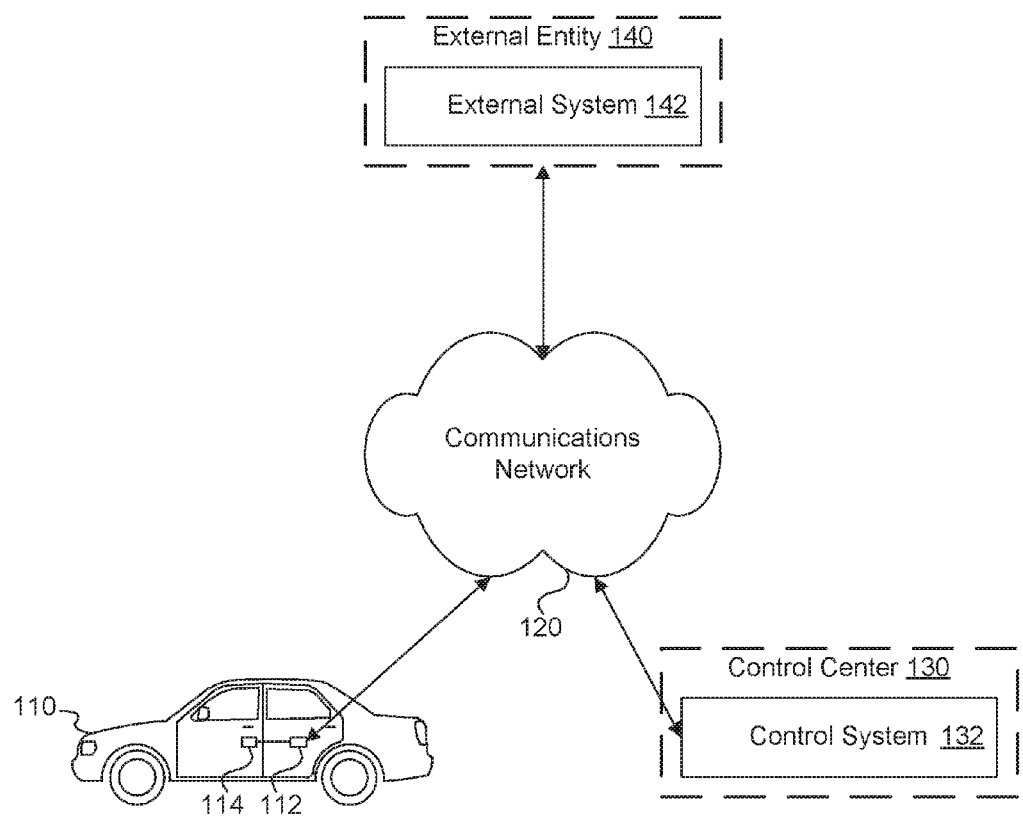
FIG. 1 depicts an example system environment for implementing embodiments consistent with the disclosed embodiments.

The disclosed embodiments relate to systems and methods for dynamically controlling sensor-based data acquisition in vehicles. The disclosed embodiments may dynamically control signals received from sensors associated with the vehicle and their respective sampling rates based on control variables driven by signal processing of the received signals and other external processes. The disclosed embodiments may apply bandwidth filters to the signals such that the filtered bandwidths are dynamically adjusted in real-time or near real-time. Moreover, the disclosed embodiments may apply event detection algorithms that are dynamically adjusted on the fly to account for current road conditions, detected events, fluctuating dangers and exposures to harm, driver behavior, and other considerations. The disclosed embodiments may modify these event detection schemes by dynamically adjusting types of signals collected, mathematical weights associated with the signals, parameters informing the relevant event detection thresholds, and the like. The disclosed embodiments may also validate detected events to ensure high data fidelity, further adjusting the input signals, bandwidths, weights, thresholds, etc. In addition, the disclosed embodiments provide systems and methods for providing signal data, filtered signal data, detected events, and other parameters to a control center for further processing. The disclosed embodiments may also provide systems and methods for processing received data at a control center to provide relevant data, information, and instructions to remote devices in communication with the sensors for further processing.

Dynamically adjusting sensor-based data acquisition in vehicles may provide one or more technical advantages. In the signal processing context, for example, it may prove advantageous to sample a smaller set of signals from vehicle sensors to improve computational efficiency without impacting accuracy. Processing or storing data associated with unnecessary signals or other information may expend computational resources on data of little value. Similar advantages may arise from sampling signals at lower or more particularized sampling rates. Further, customizing signals sampled and the accompanying sampling rates may improve the efficiency of transmitting data to, and processing the data at, other computing systems. In another example, dynamically controlling the parameters of sensor-based event detection may improve the accuracy and efficiency of these algorithms. Such dynamically adjusted event detection schemes may benefit from sampling the most relevant signals at the most relevant rates. Moreover, dynamically adjusting the thresholds and input parameters of these processes in response to real-time events may improve their efficiency and reliability. The disclosed embodiments provide at least these technical advantages by dynamically controlling sampled signals, their sampling rates, and modifying the parameters of event detection and validation schemes based on continuously updating data.

Reference will now be made in detail to embodiments of the present disclosure, examples of which are illustrated in the accompanying drawings. Where possible, the same reference numbers will be used throughout the drawings to refer to the same or like parts.

FIG. 1 depicts an example system environment 100 for implementing systems and methods consistent with the disclosed embodiments. In some aspects, environment 100 may include one or more adaptive control devices (e.g., adaptive control device 112) communicatively connected to a set of one or more sensors 114 associated with a vehicle 110. Environment 100 may include one or more control center systems (e.g., control system 132), which may be associated with one or more control centers (e.g., control center 130). Environment 100 may also include one or more external computing systems (e.g., external system 142), which may be associated with one or more external entities (e.g., external entity 140). One or more communications networks (e.g., communications network 120) may communicatively connect one or more of the components of environment 100.

Adaptive control device 112 includes one or more computing devices, data processing devices, or signal processing devices (e.g., a computing device 200 described in connection with FIG. 2) for collecting, obtaining, processing, storing, and/or transmitting information. In some embodiments, for example, adaptive control device 112 comprises a chipset with hardware and/or software applications running thereon to conduct processes consistent with the disclosed embodiments. Adaptive control device 112 may be operable to transmit and receive data or signals to other computing systems across a communications network, such as communications network 120. Adaptive control device 112 may be implemented with one or more processors or computer-based systems. Adaptive control device 112 may also be implemented with one or more data storages for storing information consistent with the embodiments described below. In some aspects, adaptive control device 112 includes one or more sensors (e.g., an accelerometer, gyroscope, compass, GNSS receiver, etc.), although such internal sensors are not required.

In certain aspects, adaptive control device 112 receives a set of signals encoding information from a set of sensors 114 (e.g., via a communications network 120 such as hardwired circuitry, NFC connection, etc.). Sensors 114 may measure any physical, temporal, operational, and/or environmental characteristic associated with vehicle 110. For example, sensors 114 may include a GNSS receiver/transceiver, GPS receiver, accelerometer, gyroscope, thermometer, hygrometer, pressure sensor, clock, CAN line or CAN bus (and/or their connected components, such as brake sensors, engine sensors, cruise control sensors, tire pressure sensors, audio systems, door sensors, navigational systems, etc.), any vehicle sensor or microcontroller, or other such sensors. Sensors 114 may measure characteristics internal to or external to the vehicle (e.g., ambient temperature, humidity, barometric pressure, etc.), as well as properties of the vehicle (e.g., position, lateral/longitudinal acceleration, elevation, etc.).

In some embodiments, adaptive control device 112 uses signals received from sensors 114 to determine or derive information associated with vehicle 110. In one example, for instance, adaptive control device 112 may determine an external temperature to vehicle 110 based on signals received from a thermometer. In another example, adaptive control device 112 may derive the speed of vehicle 110 based on its position (e.g., from a GNSS receiver), time (e.g., from a GNSS clock) and/or longitudinal acceleration (e.g., from an accelerometer). Adaptive control device 112 may also determine information such as vehicle acceleration, vehicle cornering, or external air pressure and humidity in a similar fashion (e.g., using accelerometers, gyroscopes, CAN buses, pressure sensor, and/or hygrometers, etc.). Adaptive control device 112 may derive, detect, or determine any such information from sensors 114 consistent with the disclosed embodiments. As used below, any sensor signal or vehicle characteristic immediately derived therefrom (e.g., speed, acceleration, time, cornering, ambient temperature, etc.) may be referred to as a "signal," although such description is used for illustrative purposes only and is not intended to be limiting. For example, adaptive control device 112 may receive the following signals to conduct processes consistent with the disclosed embodiments: speed, acceleration, braking, cornering, temperature, air pressure, humidity, time, position, longitudinal acceleration, lateral acceleration, throttle position, brake pedal position, yaw, pitch, roll, jerk, moisture levels, and any other type of signal described below. Adaptive control device 112 may also combine these signals to generate additional signals and/or information. For example, adaptive control device 112 may determine a driver's driving behavior based on position, acceleration, braking, cornering, and/or speed signals. In another example, adaptive control device 112 may determine ambient data (e.g., based on temperature, pressure, and/or humidity signals) or crash data (e.g., based on position, acceleration, and/or speed signals) in a similar fashion.

Environment 100 includes one or more communications networks 120. In some aspects, communications network 120 may represent any type of communication network or medium of digital communication for transmitting information between computing devices. For example, communications network 120 may include a cellular network, a satellite network, a LAN, a wireless LAN, an RF network, a Near Field Communication (NFC) network (e.g., a WiFi network), a wireless Metropolitan Area Network (MAN) connecting multiple wireless LANs, NFC communication link(s), any physical wired connection or circuitry (e.g., via an I/O port, physical circuitry, etc.), and a WAN (e.g., the Internet). In some embodiments, communications network 120 may be secured through physical encryption (e.g., line encryption), through requiring information to be encrypted on other computer systems (e.g., end encryption), and the like.

In certain aspects, communications network 120 includes any accessible network or networks interconnected via one or more communication protocols, including hypertext transfer protocol (HTTP) and transmission control protocol/internet protocol (TCP/IP). Communications protocols consistent with the disclosed embodiments also include protocols facilitating data transfer using radio frequency identification (RFID) communications and/or NFC. In some aspects, communications network 120 may also include one or more mobile device networks, such as a GSM network or a PCS network, allowing devices (e.g., adaptive control device 112, external system 142, etc.) to send and receive data via applicable communications protocols, including those described herein.

Environment 100 also includes one or more control systems 132 configured to process, store, receive, obtain, and transmit information. In certain aspects, control system 132 may reflect one or more computing systems (e.g., computing system 200, a server, a mainframe computer, etc.), and may be implemented with hardware devices and/or software instructions to perform one or more operations consistent with the disclosed embodiments (e.g., as described with reference to FIGS. 2-10). The software instructions may be incorporated into a single computer, a single server, or any additional or alternative computing device apparent to one of ordinary skill in the art. Control system 132 may also include distributed computing devices and computing systems, and may execute software instructions on separate computing systems and servers by remotely communicating over a network (e.g., communications network 120). Control system 132 may include multiple servers, and may comprise a plurality of servers or a server farm including load-balancing systems. Control system 132 may receive and transmit information to other systems within environment 100, such as adaptive control device 112 or external system 142, via any applicable network (e.g., communications network 120). Control system 132 may also implement aspects of the disclosed embodiments without accessing other devices or communication networks.

Control system 132 may include one or more data repositories, memories, or storages for storing and maintaining information. Computing systems within system environment 100 (e.g., adaptive control device 112, external system 142, etc.) may receive data stored within, and transfer data to, control system 132 consistent with the disclosed embodiments. The storages of control system 132 may also be implemented using any combination of databases or computer-readable storage mediums. For example, the storages may be maintained in a network attached storage device, in a storage area network, some combination thereof, etc.

In some embodiments, control system 132 may be associated with a control center 130. Control center 130 may reflect any entity in communication with adaptive control device 112. In some aspects, for instance, control center 130 may reflect a business, an organization, an enterprise, an educational institution, a governmental body or agency, a person, or any other entity. Control center 130 may collect, process, store, and provide information to adaptive control device 112 and other systems (e.g., external system 142) via control system 132 consistent with the disclosed embodiments.

Environment 100 may include one or more external systems (e.g., external system 142) for receiving, processing, generating, storing, and providing information. External system 142 may include its own computing systems, servers, data repositories, processors, etc., similar to that of control system 132, adaptive control device 112, or any other computing device (e.g., as described in connection with FIG. 2). For example, external system 142 may include a one or more servers, a personal computer, a laptop computer, a tablet computer, a notebook computer, a hand-held computer, a personal digital assistant, a portable navigation device, a mobile phone, a wearable device, an embedded device, a smartphone, and any additional or alternate computing device. Components of environment 100 (e.g., control system 132, adaptive control device 112, etc.) may be configured to receive information from, and provide information to, external system 142 to conduct processes consistent with the disclosed embodiments.

In some aspects, external system 142 may be associated with external entity 140. External entity 140 may represent any business, entity, educational institution, governmental body or agency, person, etc., using external system 142 to process information. For example, in one embodiment, external entity 140 may include a driver of vehicle 110. In another example, external entity 140 may reflect a business, such as a social networking site.

Figure 2:
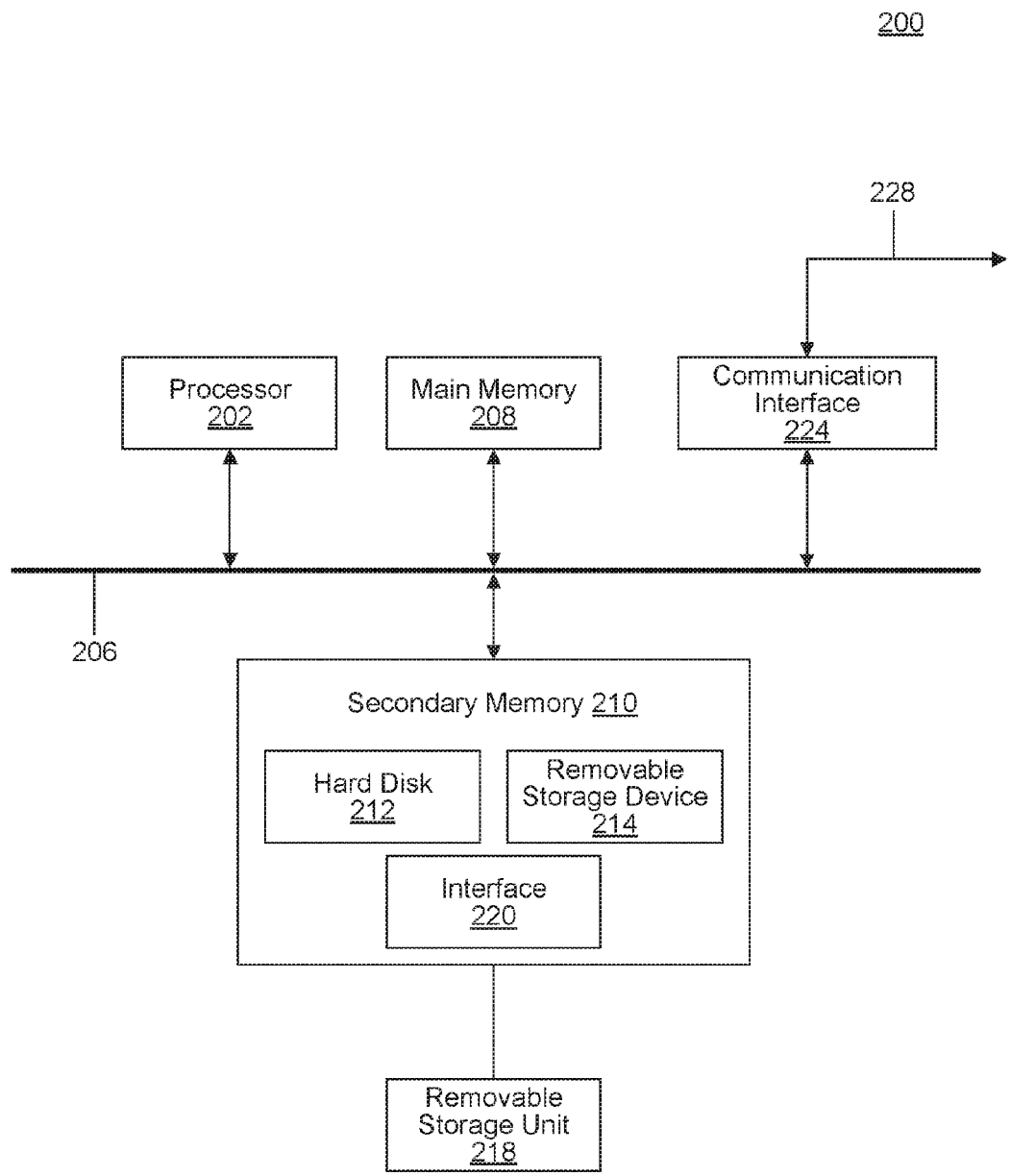
FIG. 2 depicts an example computing system for implementing processes consistent with the disclosed embodiments.

FIG. 2 depicts a block diagram of an example computer system 200 for implementing certain aspects of the disclosed embodiments. For example, in some aspects, computer system 200 may reflect computer systems associated with a device (e.g., adaptive control device 112, control system 132, external system 142, etc.) performing one or more of the processes disclosed herein. In some embodiments, computer system 200 may include one or more processors 202 connected to a communications backbone 206 such as a bus or external communications network (e.g., any medium of digital data communication such as a LAN, MAN, WAN, cellular network, WiFi network, NFC link, Bluetooth, GSM network, PCS network, I/O connection, any wired connection such as USB or hardwired circuitry, and any associated protocols such as HTTP, TCP/IP, RFID, etc).

In certain aspects, computer system 200 includes main memory 208. Main memory 208 may comprise random access memory (RAM) representing a tangible and non-transitory computer-readable medium storing computer programs, sets of instructions, code, or data executed with processor 202. When executed by processor 202, such instructions, computer programs, etc., enable processor 202 to perform one or more processes or functions consistent with the disclosed embodiments. In some aspects, such instructions may include machine code (e.g., from a compiler) and/or files containing code that processor 202 may execute with an interpreter.

In some aspects, main memory 208 may also include or connect to a secondary memory 210. Secondary memory 210 may include a disk drive 212 (e.g., HDD, SSD), and/or a removable storage drive 214, such as a magnetic tape drive, flash memory, an optical disk drive, CD/DVD drive, or the like. The removable storage drive 214 may read from and/or write to a removable storage unit 218 in a manner known to the skilled artisan. Removable storage unit 218 may represent a magnetic tape, optical disk, or other storage medium that is read by and written to by removable storage drive 214. Removable storage unit 218 may represent a tangible and non-transitory computer-readable medium having stored therein computer programs, sets of instructions, code, or data to be executed by processor 202.

In other embodiments, secondary memory 210 may include other means for allowing computer programs or other program instructions to be loaded into computer system 200. Such means may include, for example, another removable storage unit 218 or an interface 220. An example of such means may include a removable memory chip (e.g., EPROM, RAM, ROM, DRAM, EEPROM, flash memory devices, or other volatile or nonvolatile memory devices) and associated socket, or other removable storage units 218 and interfaces 220, which allow instructions and data to be transferred from the removable storage unit 218 to computer system 200.

Computer system 200 also includes one or more communications interfaces 224. Communications interface 224 may allow software and data to be transferred between computer system 200 and external systems (e.g., in addition to backbone 206). Communications interface 224 may include a modem, a network interface (e.g., an Ethernet card), a communications port, a PCMCIA slot and card, etc. Communications interface 224 may transfer software and data in the form of signals, which may be electronic, electromagnetic, optical or other signals capable of being received by communications interface 224. These signals may be provided to communications interface 224 via a communications path (e.g., channel 228). Channel 228 may carry signals and may be implemented using wire, cable, fiber optics, RF link, and/or other communications channels. In one embodiment, the signals comprise data packets sent to processor 202. For example, computer system 200 may receive signals from sensors (e.g., sensors 114) via communications interface 224 and/or communications backbone 206. Information representing processed packets may also be sent in the form of signals from processor 202 through communications path 228.

In certain aspects, the computer-implemented methods described herein can be implemented on a single processor of a computer system, such as processor 202 of computer system 200. In other embodiments, these computer-implemented methods may be implemented using one or more processors within a single computer system and/or on one or more processors within separate computer systems in communication over a network.

In certain embodiments in connection with FIG. 2, the terms "storage device" and "storage medium" may refer to particular devices including, but not limited to, main memory 208, secondary memory 210, a hard disk installed in hard disk drive 212, and removable storage unit 218. Further, the term "computer-readable medium" may refer to devices including, but not limited to, a hard disk installed in hard disk drive 212, any combination of main memory 208 and secondary memory 210, and removable storage unit 218, which may respectively provide computer programs and/or sets of instructions to processor 202 of computer system 200. Such computer programs and sets of instructions can be stored within one or more computer-readable media. In certain aspects, computer programs and sets of instructions may also be received via communications interface 224 and stored on the one or more computer-readable media.

The disclosed embodiments include systems and methods for dynamically controlling sensor-based data acquisition processes related to vehicles. These embodiments may dynamically control signals received at adaptive control device 112 from vehicle sensors 114 and their respective sampling rates based on changes to control variables. These changes in the control variables may be driven by the signals and information received from external systems (e.g., control system 132, external system 142, etc.). The disclosed embodiments may also filter the received signals with bandwidth filters that are dynamically adjusted based on the control variables. In addition, the disclosed embodiments may employ event detection to detect the occurrence or nonoccurrence of certain events. These event detection processes may be dynamically adjusted to account for changes in the control variables. The disclosed embodiments may further include using the control variables to validate detected events. The disclosed embodiments may include various remote computing devices communicating, transmitting, and receiving information generated within each process to continually update the control variables, thereby enabling each routine to be dynamically adjusted based on current data. In this manner, the disclosed embodiments may improve computational efficiency and accuracy at each of the disclosed systems due to constantly evolving sets of operative control variables. These dynamic adjustments enable the disclosed embodiments to rapidly and continuously react to informational changes, environmental factors, and information from other sources.

Figure 3:
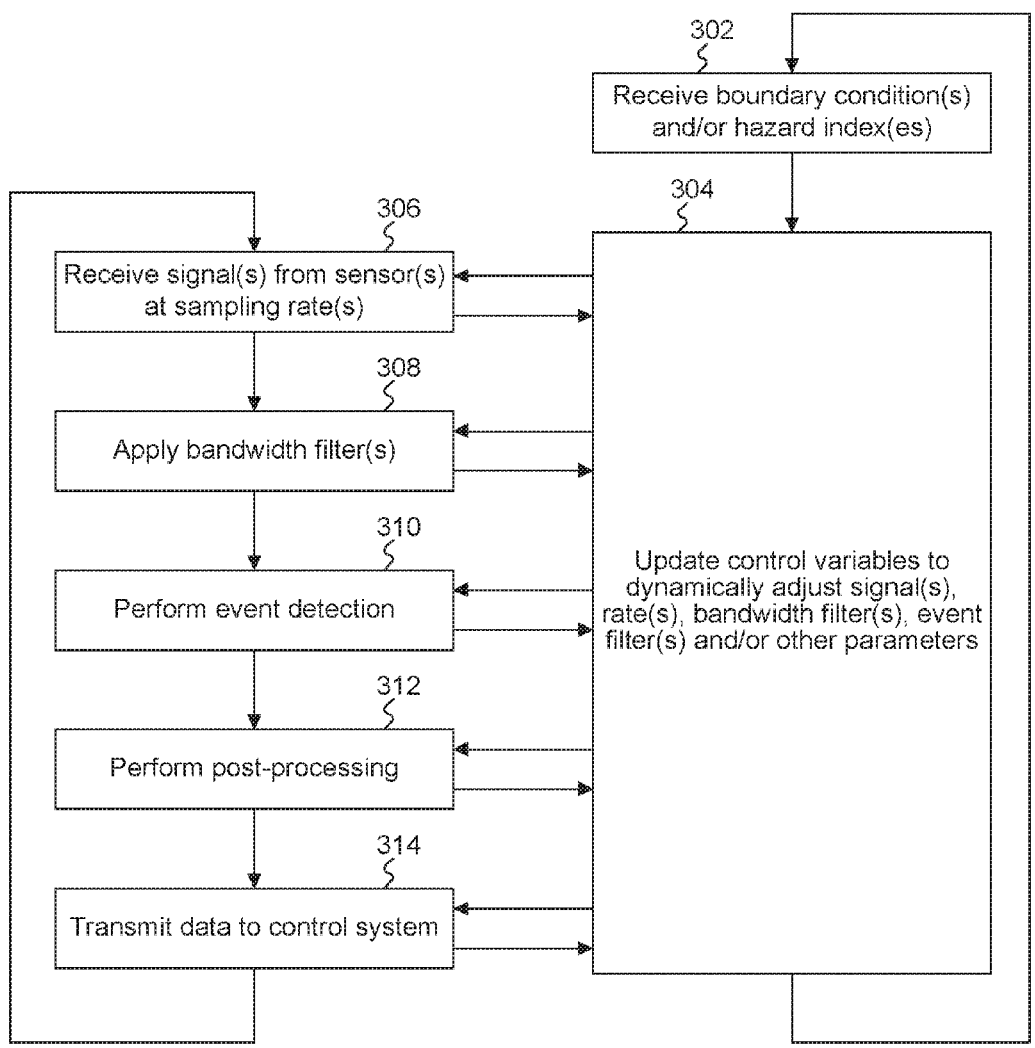
FIG. 3 depicts a flowchart for an example process for collecting and processing vehicle data that is dynamically adjusted consistent with the disclosed embodiments.

FIG. 3 depicts a flowchart of an example process 300 for collecting and processing vehicle data that is dynamically adjusted consistent with the disclosed embodiments. The embodiments described in connection with process 300 may be implemented via hardware and/or software on one or more of the components of environment 100 such as adaptive control device 112, control system 132, some combination thereof, etc. In one aspect, for example, the steps of process 300 may occur on adaptive control device 112 as described below. In other aspects, the embodiments of process 300 may be split among any number of computing systems. Moreover, certain aspects of process 300 may be reordered, rearranged, repeated, omitted, supplemented, modified, or integrated into additional processes in ways consistent with the disclosed embodiments.

In some embodiments, process 300 includes receiving a set of boundary conditions at adaptive control device 112 from an external computing system, such as control system 132 (step 302). In certain aspects, a boundary condition may reflect information associated with a condition, status, state, variable, or circumstance external to vehicle 110. This information may be stored or generated locally (e.g., on adaptive control device 112) and/or on a remote device (e.g., control system 132). In addition, this data may be based on information obtained from other external systems, such as external system 142, as well as information received or processed from adaptive control device 112 (e.g., received signals, detected events, etc.). A boundary condition may be based on current, expected (e.g., predicted), and/or historical information.

In one example, for instance, the set of boundary conditions may include a road type, path, and/or carriageway condition reflecting characteristics about the road on which a vehicle is currently traveling, will travel (e.g., based on an expected route from a navigational system or historical data), or has historically traveled in the past. Such road characteristics may include any property of the road such as its length, width, curvature (e.g., at various points along the road), number of lanes, type or classification (e.g., highway, toll road, arterial road, local road), list of included road segments or intersections, and the like.

The set of boundary conditions may also include a weather condition reflecting current, expected, or historical environmental conditions. This environmental information may include any data associated with the weather such as temperature, humidity, precipitation level or rate, barometric pressure, wind speed or direction, dew point, visibility, heat index, degree of cloud coverage (e.g., sunny, mostly cloudy, etc.), and so on. In some embodiments, the weather condition may be based on information received from adaptive control device 112 (e.g., via current or past temperature, pressure, and humidity signals). Additionally or alternatively, the weather condition may be based on information available on an external system 142.

The set of boundary conditions may include a traffic condition reflecting current, historical, and/or predicted congestion levels associated with the current or expected location of vehicle 110. This information may be based on an current or predicted route of vehicle 110 arising from, for example, information stored in a navigation system (e.g., in communication with adaptive control device 112, as part of the device itself, or as a separate external system 142, etc.) and/or a driver's historically favored routes or roads (discussed further below). By way of example, the traffic condition may reflect congestion levels associated with a current active route of vehicle 110 (e.g., based on an on-board navigation system, a routing application on driver's mobile device 142, data stored within adaptive control device 112, etc.) with expected detours to account for the driver's historical preference for certain roads or road types.

In some embodiments, the set of boundary conditions may also include an average speed map condition reflecting an average speed of vehicles within some distance or proximity range of vehicle 110 (e.g., 50 feet, 100 feet, 500 feet, etc.). In some aspects, the average speed map condition may also be based on a current, historical, or predicted average speed of vehicles associated with the current location of vehicle 110 (e.g., a second proximity range, a road, a road segment, etc.).

The set of boundary conditions may further include a black point condition reflecting a path, route, road segment, intersection, point, location, etc., in which the probability of being involved in an accident is high (e.g., the probability of an accident exceeds a threshold). In some aspects, the black point condition may be based on a current, historical, or expected location or route of vehicle 110, such as those described herein. The black point condition may also reflect accident information stored on a system in environment 100 (e.g., adaptive control device 112, external system 142 such as a highway patrol system, etc.). The accident information may include data such as historical accident rates associated with the location, congestion levels (historical, current, expected, etc.) associated with the location and/or those nearby, and other information consistent with the disclosed embodiments. In some embodiments, the black point condition may also incorporate accident information associated with other locations and paths. For example, the black point condition may arise as a function of a location's accident rate, congestion level, etc., compared to those of similar locations (e.g., by road type, etc.), nearby locations, locations along a particular route, and other such parameters. In one illustrative example, for instance, the black point condition may reflect road segments or other locations having an accident rate higher than a local or national average for those on a similar location.

The set of boundary conditions may include a standard driver condition reflecting an average or aggregate driver behavior (e.g., acceleration, position, braking, cornering, and/or speed profiles) across several or all drivers. In some embodiments, the standard driver condition may include behavior information associated with drivers in general (e.g., across all weather conditions, road types, etc.). In other embodiments, the standard driver condition may be constrained to particular dimensions such as particular roads, road types, road segments, curves or intersections, time of day, weather conditions, vehicle make/model/type, driver age group, etc. In some aspects, the set of drivers may be limited to those associated with an adaptive control device 112.

Similarly, the set of boundary conditions may include a current driver condition reflecting an average or aggregate driver behavior (e.g., the driver's acceleration, position, braking, cornering, and/or speed information) for the driver currently operating vehicle 110. This information may embody the driver's behavior generally (e.g., across all dimensions) or within certain dimensions (e.g., along a particular road, road segment, curve, time of day, weather condition, etc., as described above). The current driver condition may be based on, for example, information received from adaptive control device 112 and/or driver credential information (e.g., provided to the adaptive control device) identifying the current driver of vehicle 110.

In some aspects, the set of boundary conditions may also include a driver device condition reflecting information associated with or received from an electronic device (e.g., an external system 142) associated with the driver. This information may include current, expected, or historical biorhythm data (e.g., sleep information, heart rate, blood pressure, steps taken) and/or device usage data (e.g., information associated with call logs, messaging or e-mail, calendars, planned navigational routes, music listened to, websites visited, software application data, etc.).

The set of boundary conditions may also include a usual route condition reflecting information associated with routes, road types, roads, and/or road segments typically favored by a driver of vehicle 110. Such information may be based, for example, on historical routing and driving information tracked by adaptive control device 112, similar information stored on navigational systems associated with vehicle 110 or the driver (e.g., on external system 142, such as a mobile phone), and the like. In one example, for instance, the usual route condition may reflect that a driver typically avoids highways, does so for particular segments of particular highways, favors one road or route over another, and so forth.

The set of boundary conditions may also include a social network condition reflecting information obtained from one or more social networks associated with a driver of vehicle 110. This social network information may include data such as the time and place of posts; the content of such posts (e.g., parsed by a lexical or semantic process to extract relevant information, such as interests, emotions, future or past events, etc.); indicated interests, "likes," or favorites (e.g., music, movies, hobbies, sports, people, politics, etc.); any of the forgoing information for friends, followers, etc.; biographical or demographic information (e.g., birthday, degree(s), degree institution(s), residence, employer or employment type, religion, relationship status, etc.); shared information (e.g., shared news articles); and/or any other information extractable from any social network known to one of ordinary skill in the art. The computing systems obtaining such information (e.g., control system 132) may do so over a network (e.g., communications network 120) based on information stored, hosted, and managed by the social network (e.g., as external system 142).

In some aspects, the set of boundary conditions may also include a claim history condition reflecting information associated with one or more insurance claims associated with vehicle 110. This claim information may include data such as a number of claims, a frequency of the claims, an amount associated with the claims (e.g., each individual claim amount, an average, a sum, a median, etc.), a nature of the claims, and other such information.

In certain embodiments, process 300 may include receiving a set of hazard indices associated with vehicle 110 or a driver thereof (step 302). In some aspects, a hazard index may reflect a measure or degree of exposure to danger associated with a driver or vehicle 110 at a specific point in time. A hazard index may incorporate historical, current, and/or predicted information, and may be associated with a past, current, or future time period (e.g., a driver's predicted exposure to hazard in the future). A hazard index may be based on, for example, one or more boundary conditions received or generated by control system 132 and/or information received from adaptive control device 112 (e.g., any signal or other information described in connection with FIGS. 3-8). In some aspects, a hazard index may reflect a driver's exposure to danger based on that driver's driving behavior (e.g., based on speed, acceleration, corning, breaking, and/or position signals received by adaptive control device 112), attention (e.g., based on information associated with a driver device condition, social network condition, average speed map condition, such as whether the driver is sending text messages, etc.), and/or environment (e.g., based on a weather condition or relevant signals received via adaptive control device 112 such as temperature, visibility, precipitation, moisture levels, etc.). A hazard index may be generated and updated using any process consistent with the disclosed embodiments, such as those described in connection with FIG. 8.

In some aspects, process 300 may include generating, updating, modifying, adding, changing, and/or deleting one or more control variables in a set of control variables managing various aspects of the disclosed embodiments (step 304). In certain aspects, the set of control variables may govern how adaptive control device 112 and/or control system 132 collect, handle, and process data. For example, the set of control variables may define certain parameters, inputs, and thresholds of routines described in connection with FIGS. 3-8, such as the particular signals sampled from vehicle sensors 114, the rates at which adaptive control device 112 samples the selected signals, and/or the various parameters, inputs, and thresholds in processes associated with bandwidth filtering, event detecting, and post-processing, among other things. Thus, in some aspects, the control variables define the inputs and other information collected (e.g., signals sampled, external information retrieved, etc.) as well as the processes using this information (e.g., by changing filters, weights, and thresholds) to determine whether an event has occurred. These processes are described in greater detail below. The set of operative control variables (e.g., the control variable(s) active at any given time) may be based on the set of boundary conditions, the set of hazard indices, and/or any information described herein. By way of example, the set of control variables may be based in part on signals received in adaptive control device 112 from vehicle sensors 114, the detection of a particular event, application of a particular filter, current weather conditions, information on social media, expected routes a driver is predicted to take, the curvature of a road segment, and so on. The set of control variables may be stored in memory in any suitable computing device, such as a memory of adaptive control device 112 and/or control system 132.

Because the control variables may govern how adaptive control device 112 collects and processes data in some aspects, changes to an operative set of control variables (e.g., creation of a new variable, deletion or modification of an existing variable, etc.) may cause a resulting change to the way adaptive control device 112 processes information. For example, a change to a set of operative control variables may cause a change to the signals sampled with adaptive control device 112, their corresponding sampling rates, applied bandwidth filters, event detection or validation thresholds, and/or any other variable parameter consistent with the disclosed embodiments. Adaptive control device 112 may automatically and continually detect changes to the set of control variables to dynamically adjust the processes disclosed herein.

The set of control variables may include a set of local control variables and/or a set of external control variables. External control variables may reflect control variables generated, updated, and/or influenced by information external to adaptive control device 112. For example, in some aspects, the external control variables may be based on a set of boundary conditions and/or a set of hazard indices received from control system 132. In one embodiment, for instance, the set of external control variables may be based on historical, current, or expected weather conditions, traffic patterns, road and path information, average driver behavior, or any other information associated with a boundary condition or hazard index. Additionally or alternatively, the set of external control variables may be based on other types of information obtained or received from external system 142 or control system 132. In one aspect, for example, adaptive control device 112 may receive an instruction from control system 132 to add, modify, delete, etc., an external control variable with or without any corresponding change to a boundary condition or hazard index. External control variables may be generated locally on adaptive control device 112 (e.g., in response to information received from control system 132), or on an external system (e.g., control system 132) and transmitted to the adaptive control device.

Local control variables may reflect control variables generated, updated, and/or influenced by information local to adaptive control device 112. In some aspects, local control variables may be generated and updated on adaptive control device 112 and may be based on any information consistent with the embodiments described in connection with FIGS. 3-7. For example, adaptive control device 112 may generate or update a set of local control variables based on a set of signals received from vehicle sensors 114 (e.g., information encoded in the set of signals, the set of signals sampled, etc.). In one illustration, adaptive control device 112 may generate or update local control variables based on a current temperature signal from a temperature sensor. In another example, adaptive control device 112 may update a set of local control variables based on a driver's historical driving behavior as monitored by the adaptive control device (e.g., based on historical acceleration, position, braking, cornering, and/or speed signals). The set of local control variables may also comprise control variables created from processes conducted on adaptive control device 112. For example, the set of local control variables may include control variables generated from an applied bandwidth filter, an event detection analysis, and/or post-processing, as described in reference to FIGS. 5-7. In certain embodiments, the sets of local and external control variables are not mutually exclusive. For example, the set of control variables may be updated based on a driver's historical driving behavior as measured by signals received at adaptive control device 112 as well as a boundary condition received from control system 132.

In some embodiments, process 300 may include receiving at adaptive control device 112 a set of signals associated with a set of vehicle sensors 114 (step 306). These signals may relay information associated with the characteristics measured with (or derived from) the sensors 114, such as speed, acceleration, breaking cornering, temperature, air pressure, position, yaw, pitch, roll, and/or any other information associated with sensors consistent with the disclosed embodiments (e.g., any vehicle component connected to a CAN bus, such as engine or tire pressure sensors). In some embodiments, the set of signals received or sampled may be based on a set of control variables stored on adaptive control device 112. For example, the set of control variables may define the set of signals to sample based on the signals required for a bandwidth filter analysis, event detection analysis, and/or event validation analysis as further described in reference to FIGS. 5-7. By way of example, the control variables may instruct adaptive control device 112 to sample signals associated with cornering, raw, pitch, and/or roll in order to determine or validate the occurrence of a cornering event. Adaptive control device 112 may determine the set of signals to sample based on the set of stored or received control variables, and may sample the identified signals in the set of signals consistent with this determination.

In some aspects, adaptive control device 112 may modify or adjust a set of sampled signals upon detecting a change in a set of operative control variables (step 304). Changes to the set of operative control variables may adjust the types, number, and/or identity of signals sampled with adaptive control device 112. Because the set of control variables may continually or periodically change over time, this arrangement enables adaptive control device 112 to dynamically adjust the set of signals sampled from sensors 114. Adaptive control device 112 may adjust the set of signals sampled via hardware and/or software executed by one or more processors. For example, adaptive control device 112 may adjust a first set of sampled signals by switching off a previously sampled signal (e.g., a signal in the first set of signals) and/or switching on a previously unsampled signal (e.g., a signal not in the first set of signals) via hardware, thereby sampling a second, different set of signals. Such hardware may take the form of, for example, switches in embedded circuitry of adaptive control device 112. In another example, adaptive control device 112 may disable or enable these signals via software by, for instance, reducing the value of a selected signal to zero or removing such a zero condition from another signal.

Adaptive control device 112 may sample each signal in a set of signals at a respective sampling rate (step 306). These sampling rates may vary among the received signals and may be defined in a set of control variables. For example, adaptive control device 112 may sample a first signal (e.g., acceleration, angular speed) at a first rate (e.g., 6 kHz) and may sample a second signal (e.g., external temperature) at a second rate (e.g., 1 Hz). A sampling rate may be based in part on the type of signal received. In the example above, for instance, adaptive control device 112 may sample an acceleration signal more often than a temperature signal. Adaptive control device 112 may determine the respective sampling rate for each signal in the set of signals based on the set of control variables.

In some embodiments, a detected change to the set of one or more operative control variables may adjust one or more of the sampling rates in the set of sampling rates (step 304). Adaptive control device 112 may determine how to adjust a sampling rate for a particular signal based on detecting the change(s) to the set of control variables. In some embodiments, the changes in the set of control variables may reflect that a particular signal or condition has become more or less important for a process consistent with the disclosed embodiments (e.g., a routine described in connection with FIGS. 5-8). For example, the set of control variables may change upon detecting harsher weather conditions to cause adaptive control device 112 to sample signals associated with weather information (e.g., temperature, moisture levels, visibility, precipitation rate, etc.), speed information, etc., more frequently than in calmer, dryer conditions.

In certain embodiments, adaptive control device 112 transmits the set of signals (e.g., the signal values themselves and/or the type of signals sampled), the set of sampling rates, and/or other information related to the set of sampled sensors (e.g., the sensors associated with the received signals) to another computing system for further processing. This processing may include processes such as those described in connection with FIG. 8 in control system 132. For example, control system 132 may receive a set of signals and their sampling rates outputted from adaptive control device 112, adjust one or more boundary conditions and/or hazard indices in response to the received information, provide the updated set of boundary conditions to the adaptive control device (step 302), which may cause the adaptive control device to adjust the operative set of control variables (step 304), which in turn may cause the adaptive control device to change the set of sampled signals and/or their sampling rates (step 306), among other things. Additionally or alternatively, adaptive control device 112 may generate or update the set of operative control variables based on information encoded in the set of signals sampled and other information consistent with the disclosed embodiments.

In some embodiments, adaptive control device 112 applies a set of bandwidth filters to the received signals to reduce noise or other artifacts (step 308). Passing the signals through the bandwidth filter(s) may create a set of filtered signals with a higher signal-to-noise ratio (SNR) than the unfiltered signals. Applying the bandwidth filters may occur via hardware (e.g., via switches, capacitors, resistors, and other circuitry) and/or software (e.g., executing instructions with a processor) to create the desired effect. Adaptive control device 112 may apply the set of bandwidth filters in ways consistent with the disclosed embodiments, such as the bandwidth filtering process described in connection with FIG. 5. For example, adaptive control device 112 may determine how to apply the set of bandwidth filters based on a set of control variables stored in memory. Adaptive control device 112 may detect changes in the set of control variables and dynamically adjust how it applies the set of bandwidth filters (steps 304 and 308). In some embodiments, adaptive control device 112 may output or transmit information associated with the bandwidth filtering process (e.g., data consistent with the embodiments described in connection with FIG. 5) to control system 132 for further processing (e.g., such as those described in reference to FIG. 8). In one example, control system 132 may receive information from adaptive control device 112 related to a bandwidth filtering process, update a boundary condition or hazard index based on the received information, and send the updated boundary condition or hazard index to the adaptive control device (step 302). As disclosed herein, such a change to the boundary conditions and/or hazard indices may cause a change to the set of operative control variables (step 304), which in turn may dynamically adjust how adaptive control device 112 applies the set of bandwidth filters (step 308). Further, adaptive control device 112 may itself update the set of control variables based on information produced during the bandwidth filter process.

Process 300 includes performing an event detection analysis on a set of signals, such as a set of filtered signals produced in step 308, a set of unfiltered signals from sensors 114, etc. (step 310). Adaptive control device 112 may perform the event detection analysis to determine the occurrence or nonoccurrence of an event, as described in further detail below. In certain aspects, this determination may include comparing a set of event thresholds to the set of signals and generating a Boolean-type response based on the comparison. Adaptive control device 112 may conduct the event detection using any processes consistent with the disclosed embodiments, such as the event detection processes described in connection with FIG. 6. For example, adaptive control device 112 may determine how to apply a set of event filters to the set of signals, including parameters affecting the event thresholds of the event filters (e.g., mathematical weights, combinations of signals and event factors, etc.), based on a set of control variables. Further, adaptive control device 112 may detect a change to the set of control variables and dynamically adjust the event detection routines accordingly (steps 304 and 310). Adaptive control device 112 may also output or transmit information associated with the event detection process to control system 132 for further processing, such as the processing described in connection with FIG. 8 or those above. Adaptive control device 112 may also process the results of the event detection to update the set of operative control variables.

Process 300 includes performing post-processing in response to detecting or not detecting an event (step 312). In certain aspects, this post-processing may reflect a validation process confirming that a detected event has or has not occurred, such as the validation process described in reference to FIG. 7. In some embodiments, this validation process may include monitoring select signals for a period of time following a detected event and comparing those signals to a set of validation thresholds. In some aspects, adaptive control device 112 may determine the inputs and parameters (e.g., mathematical weights, signals sampled, validation thresholds, etc.) of such post-processing routines based on a set of control variables. In addition, adaptive control device 112 may detect a change in the set of control variables and dynamically adjust the post-processing routines accordingly (steps 304 and 312). In certain embodiments, adaptive control device 112 may transmit information associated with the post-processing to another computing system (e.g., to control system 132 upon validating an event) validated to conduct further processing consistent with the disclosed embodiments, such as those described in reference to FIG. 8 or above.

In some aspects, process 300 may include outputting event data or transmitting it to control system 132 from adaptive control device 112 (step 312). Event data may include information associated with the signal receiving, bandwidth filtering, event detection, and/or post-processing steps. For example, event data may include an indication that adaptive control device 112 has detected an event, validated an event, not detected an event, etc. Event data may also include information associated with these steps such as, for example, the set of signals sampled, the set of sampling rates, the event or validation thresholds used in the detection and validation steps, that an event has occurred or has been validated, or any other information associated with FIGS. 3-8. Event data may take any appropriate form for conveying information, such as a signal, a computer file, a record, an electronic report, an e-mail, text message, etc.

Adaptive control device 112 may transmit the event data to control system 132 via communications network 120. In some aspects, control system 132 may receive the event data and conduct further processing consistent with the disclosed embodiments, such as the processes described above or in connection with FIG. 8. For example, control system 132 may receive the event data, determine or modify a set of boundary conditions, collect or generate information related to such boundary conditions, and provide the boundary conditions and related information to adaptive control device 112 (step 302). These updated boundary conditions and information may adjust one or more control variables governing adaptive control device 112 (step 304), which in turn may cause a dynamic adjustment to the disclosed embodiments as described herein (e.g., any routine in connection with steps 306-314).

Figure 4:
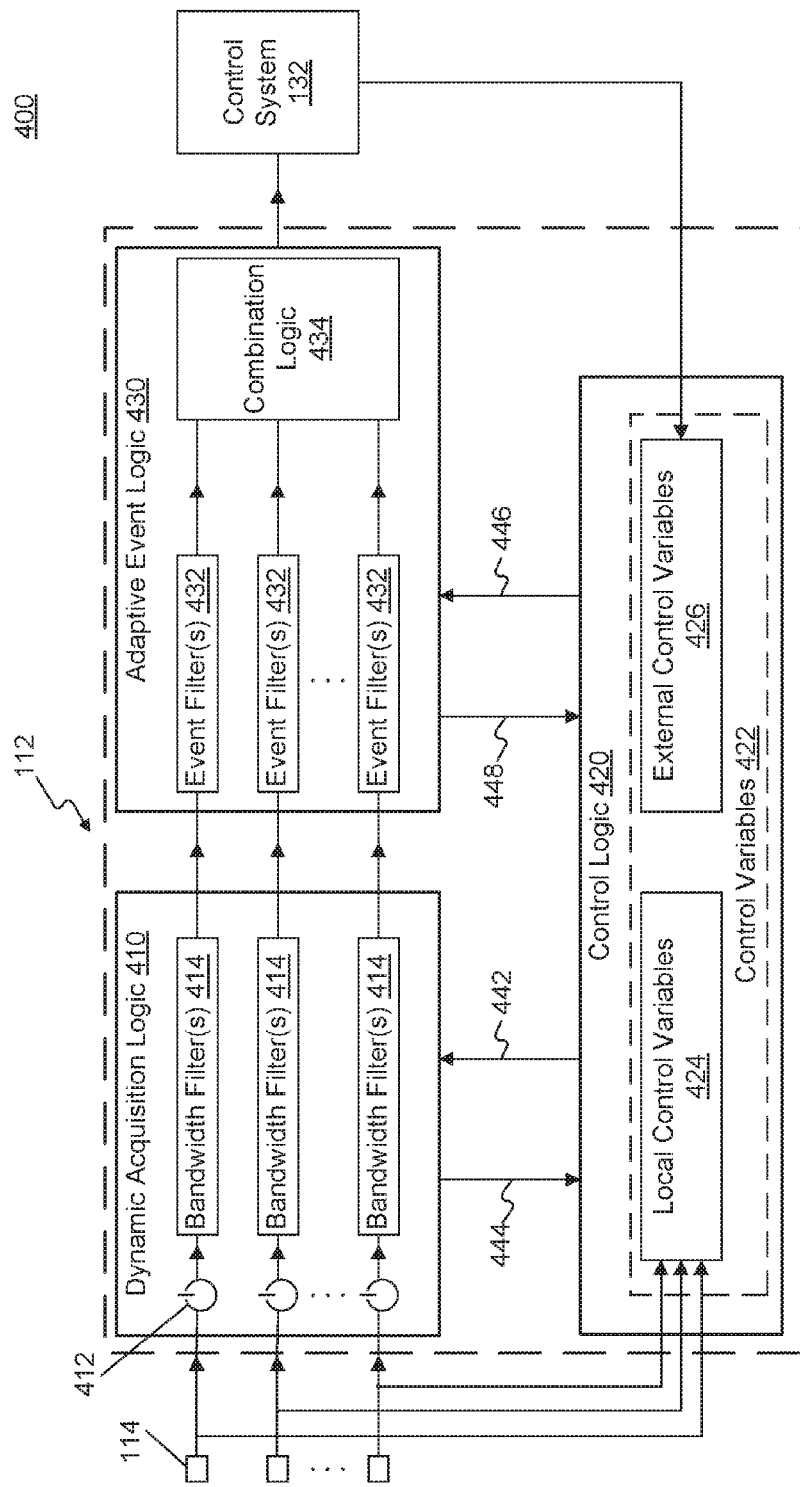
FIG. 4 depicts a block schematic of an example adaptive control device and data flow consistent with the disclosed embodiments.

FIG. 4 depicts a block schematic 400 of an example adaptive control device 112 in communication with other components consistent with the disclosed embodiments. FIG. 4 provides a general overview of the signal processing and data flow consistent with certain aspects of the disclosed processes. In some aspects, the embodiments described in connection with FIG. 4 may be implemented via hardware (e.g., comprising circuitry for signal transmission, filtering, etc.) and/or software (e.g., executed by processors onboard adaptive control device 112, control system 132, etc.).

As shown in FIG. 4, adaptive control device 112 may receive a set of signals from a set of vehicle sensors 114 with control logic 420. In certain aspects, control logic 420 may reflect hardware and/or software for generating, updating, modifying, and/or managing a set of control variables 422 governing processes within adaptive control device 112. The control variables 422 of control logic 420 may comprise any type or instance of control variable consistent with the disclosed embodiments. In some aspects, for instance, the set of control variables 422 may include a set of local control variables 424 and a set of external control variables 426. As explained above, and as depicted in FIG. 4, the set of local control variables 424 may be based in part on the signals received from sensors 114. In certain embodiments, control logic 420 may generate the set of local control variables 424 and/or external control variables 426 using any suitable process consistent with the disclosed embodiments, such as those disclosed in connection with FIGS. 3-8. Adaptive control device 112 may store the set of control variables 422 in memory.

In some aspects, control logic 420 may generate and send a control signal 442 to dynamic acquisition logic 410 based on set of control variables 422 or a subset thereof. Dynamic acquisition logic 410 may reflect hardware and/or software for dynamically acquiring, sampling, and filtering a set of signals from sensors 114 based on the control signal 442 received from control logic 420. In certain aspects, control signal 442 may reflect an instruction to sample a particular set of signals, each at a respective sampling rate. Dynamic acquisition logic 410 may sample the selected set of signals from sensors 114 in accordance with control signal 442 (e.g., by sampling the instructed signals at the appropriate rate). For example, dynamic acquisition logic 410 may switch off any signal not included in the instruction of control signal 442 via switches 412. Similarly, dynamic acquisition logic 410 may switch on the signal(s) designated in the control signal 442 with switches 412 so that those signal(s) are included in the sampled set of signals. Dynamic acquisition logic 410 may also switch off and on the appropriate signals via software processes executed by internal processors on adaptive control device 112, as explained above. In some embodiments, dynamic acquisition logic 410 may also switch on and off the signals passed to control logic 420 from sensors 114 in a similar fashion (e.g., based on the same or different set of control variables 422), although such manipulation is not required. Additionally or alternatively, dynamic acquisition logic 410 may perform aspects of the signal receipt and sampling processes as described herein, such as those described in reference to FIG. 3.

In some embodiments, dynamic acquisition logic 410 may send one or more of the sampled signal(s) through a set of bandwidth filters 414. As explained above and below in reference to FIG. 5, the set of bandwidth filters 414 may reduce noise and other artifacts in the sampled signals. In some embodiments, dynamic acquisition logic 410 may pass all of the sampled signals through the set of bandwidth filters 414. In other embodiments, dynamic acquisition logic 410 may subject only a subset of the sampled signals to the set of bandwidth filters 414 based on instructions contained in a control signal 442 from control logic 420 (e.g., the same or different control signal described above). The control signal 442 may include other information and instructions consistent with the disclosed embodiments.

In certain aspects, dynamic acquisition logic 410 provides a response signal 444 to control logic 420. The response signal 444 may include any information generated or processed by acquisition logic 410. For example, the response signal 444 may include information associated with the set of signals sampled (e.g., the signals themselves, the sensors sampled, the sampling rates, etc.), the signals disabled or enabled, and/or any information associated with the bandwidth filters (e.g., as disclosed in connection with FIG. 5). In some aspects, control logic 420 may receive the response signal 444 and update the set of control variables 422 accordingly. For example, control logic 420 may determine to modify, add, and/or delete one or more control variables 422 (e.g., by changing the set of local control variables 424) based on the information provided in the response signal 444. This change in control variables 422 may cause additional changes and dynamic adjustments to adaptive control device 112 and its processes consistent with the disclosed embodiments. By way of example, control logic 420 may receive a bandwidth-filtered cornering signal from dynamic acquisition logic 410 in response signal 444 indicating that a driver of vehicle 110 is cornering within standard ranges (e.g., based on boundary condition information, filtered signal data, etc.). Control logic 420 may then update the control variables 422 so that, when this update is detected in adaptive control device 112, dynamic acquisition logic 410 samples the cornering signal at a lower sampling rate, not at all (e.g., the cornering signal is switched off), etc.

As depicted in FIG. 4, adaptive control device 112 passes the sampled signals from dynamic acquisition logic 410, filtered or unfiltered, through adaptive event logic 430. In some embodiments, adaptive event logic 430 reflects an event detection process for determining the occurrence or nonoccurrence of an event based on a set of received signals. Adaptive event logic 430 may take the form of hardware and/or software components consistent with the disclosed embodiments, such as those described in reference to FIG. 6.

In some aspects, adaptive event logic 430 may pass the set of signals through a set of event filters 432. In certain embodiments, an event filter 432 may reflect a set of instructions for generating an event threshold for a particular set of signals and comparing those signals to the event threshold to generate a Boolean-type response. In these embodiments, the event threshold may represent a critical value or measure of one or more signals defining when the event or a subevent (e.g., some subsidiary determination necessary but not sufficient to determine the occurrence of the event) is deemed to have occurred. An event filter 432 may instruct adaptive event logic 430 how to generate an event threshold given a particular set of input signals (e.g., speed, acceleration, and/or cornering), and then compare the signal set to the generated event threshold to generate a Boolean response. By way of example, event filter 432 may output a true-type Boolean response when a signal such as a speed signal exceeds an event threshold established with the event filter. The event filter 432 may compare a single signal to the event threshold or a combination of several signals to the event threshold. These embodiments are described in further detail in reference to FIG. 6. In some aspects, the event filter 432, its defined event thresholds, its set of signals processed, etc., may be driven by a set of control variables stored within adaptive control device 112.

Adaptive event logic 430 may combine the set of signals and/or the results for each event filter 432 with combination logic 434. Combination logic 434 may reflect a representation of an event (e.g., an event representation) in terms of a logical or mathematical combination of one or more signals and/or outputs from event filters 432. That is, the event representation may identify how adaptive control device 112 (or control system 132) determines whether an event occurs based on a mathematical or logical combination of signals and/or outputs from event filters 432. Combination logic 434 may operate on a set of signals or a set event filter results in ways consistent with the disclosed embodiments, such as those described in reference to FIG. 6.

As shown in FIG. 4, for example, combination logic 434 may combine the results of a set of event filters 432 in a logical expression (e.g., based on the event representation) to generate a Boolean-type indication of whether the event has occurred. The logical expression may employ any permutation of AND, NOT, XOR, and/or OR operators reflecting the event representation in logical terms. By way of example, given three subevent results $SR_1$, $SR_2$, and $SR_3$ from three event filters 432, combination logic 434 may define that the event E has occurred when ($SR_1$ AND $SR_2$) OR (NOT $SR_3$) is true, that is, the event representation may be:

$$E = (SR_1 \wedge SR_2) \wedge \neg SR_3.$$

In another embodiment not depicted in FIG. 4, combination logic 434 may combine a set of filters in one or more mathematical expressions reflecting an event representation of the event (or subevent) E in mathematical terms before passing the signals through event filters 432. The results of the combination logic 434 may then pass through an event filter 432 to determine whether E has occurred. For example, given a set of signals x, combination logic 434 may generate or reflect an event representation of E as some function of x, which is then compared to an event threshold T defined by event filter 432 so that E is deemed to occur when:

$$f(x) > T.$$

In still other embodiments, adaptive event logic 430 may employ several such combination logics 434 and event filters 432 in even more complex expressions of the event representation. These embodiments are described in further detail below in connection with FIG. 6.

As shown in FIG. 4, the parameters of the event filter(s) 432 and combination logic 434 may be based on the set of control variables 422 in control logic 420. In some aspects, for example, control logic 420 may instruct adaptive event logic 430 of the parameters of the event filters (e.g., how each event filter generates an event threshold given a defined set of signals, the set of signals sampled in the event filter, etc.), combination logic 434 (e.g., the representation of the event in mathematical or logical terms), and how they interact (e.g., the order and inputs for the event filters and combination logic) via control signal 446. In these aspects, control signal 446 may thus reflect an instruction to adaptive event logic 430 for generating a Boolean response to whether an event has occurred given a set of signal inputs. In certain aspects, adaptive event logic 430 may then employ the set of event filter(s) 432 and/or combination logic 434 consistent with control signal 446.

In some aspects, adaptive event logic 430 may transmit a response signal 448 to control logic 420. The response signal 448 may include any information generated or processed by adaptive event logic 430. For example, the response signal 448 may include information associated with whether an event has occurred, whether a subevent has occurred, information used to calculate the event threshold(s), or any other information consistent with the event detection processes described herein. In certain embodiments, control logic 420 may receive the response signal 448 and update the set of operative control variables 422 accordingly. For example, control logic 420 may determine to modify, add, and/or delete one or more control variables 422 (e.g., changing the set of local control variables 424) based on the information provided in response signal 448 (e.g., whether an event has occurred). This change in control variables 422 may cause additional dynamic adjustments to adaptive control device 112 and its processes consistent with the disclosed embodiments. By way of example, control logic 420 may receive a response signal 448 from adaptive event logic 430 indicating that a certain event (e.g., a speeding event or crash event) has occurred. Control logic may then update the control variables 422 so that, when this change is detected in adaptive control device 112, dynamic acquisition logic 410 samples particular signals (e.g., speed) at particular rates, event thresholds are decreased in adaptive event logic 430 (e.g., to account for elevated hazard levels), and the like.

At any step of the foregoing process, adaptive control device 112 may transmit the generated data or associated information to control system 132 (or external system 142) for additional processing consistent with the disclosed embodiments. For example, as depicted in FIG. 4, adaptive control device 112 may transmit the results of the event detection process of adaptive event logic 430 to control system 132. In some embodiments, control system 132 may receive the transmitted information to conduct additional processes disclosed herein (e.g., as described in connection with FIG. 8). For example, control system 132 may modify, add, and/or delete one or more boundary conditions, update one or more hazard indices, or obtain additional information from external system 142, based on the information received from adaptive control device 112. Control system 132 may provide these updated boundary conditions, hazard indices, and/or additional information to adaptive control device 112 to conduct further processing thereon. In one example, adaptive control device 112 may use the received data to update one or more control variables 422 (e.g., by updating a set of external control variables 426 based on new boundary condition information and/or hazard indices). In another example, adaptive control device 112 may use information received from control system 132 to generate one or more event thresholds.

Figure 5:
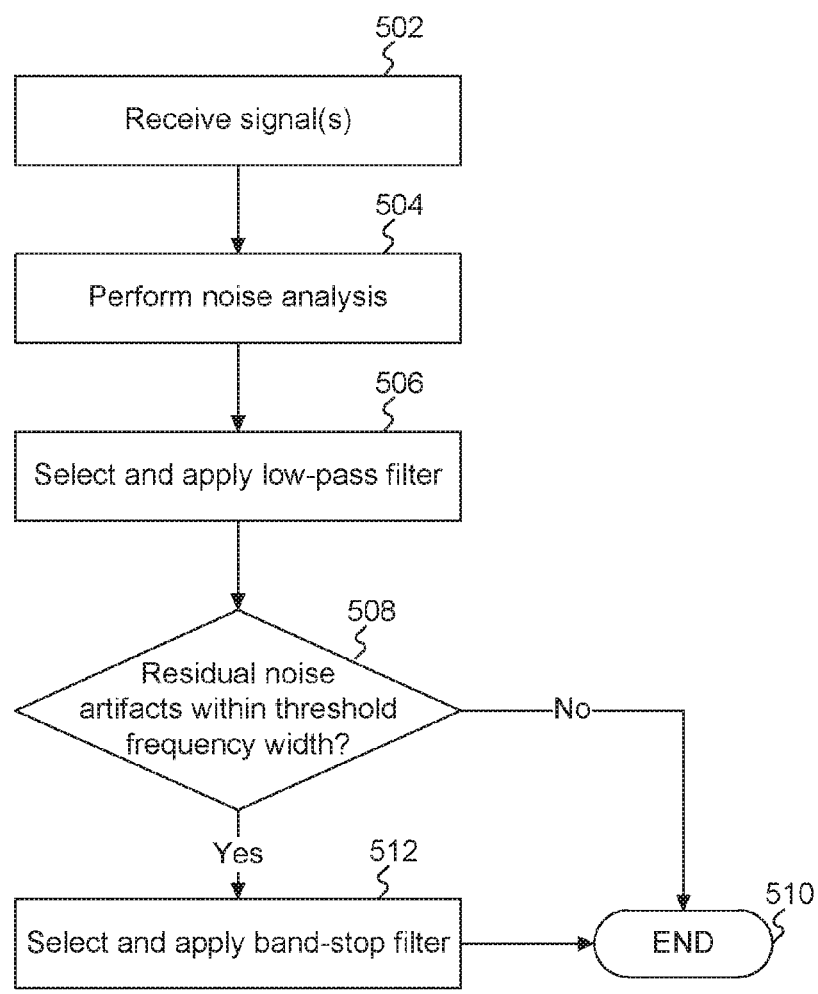
FIG. 5 depicts a flowchart for an example bandwidth filter process consistent with the disclosed embodiments.

FIG. 5 depicts a flowchart for an example bandwidth filter process 500 consistent with the disclosed embodiments. Aspects disclosed in connection with process 500 may be implemented via hardware and/or software on one or more computing systems of environment 100, such as adaptive control device 112 and control system 132. Certain aspects of process 500 may be reordered, rearranged, repeated, omitted, supplemented, modified, or integrated into additional processes in ways consistent with the disclosed embodiments. For example, embodiments described in connection with process 500 may be implemented in adaptive control device 112 to apply a set of bandwidth filters, such as those described in connection with step 308 of FIG. 3 or within dynamic acquisition logic 410 of FIG. 4, etc.

In some aspects, process 500 receives a set of signals associated with a set of vehicle sensors 114 (step 502). The received signals may take any form and may reflect the output of any sensor 114 or derived signal consistent with the disclosed embodiments. By way of example, process 500 may receive a set of four signals comprising a breaking, cornering, position, and longitudinal acceleration signal. Any number of signals may be received in this manner.

Process 500 may perform a noise analysis on one or more of the received (noisy) signals (step 504). In some aspects, process 500 may perform the noise analysis on every received signal. In other aspects, process 500 may determine whether to perform a noise analysis on the received signal (e.g., a noisy signal) based on the signal type (e.g., the parameter the signal is measure) and/or a set of control variables 422 stored on adaptive control device 112. In some embodiments, process 500 may perform the noise analysis on signal levels averaged over some time increment, such as one or five seconds.

In certain embodiments, the noise analysis may include performing a Fourier analysis on the subject noisy signal(s). Such Fourier analysis may include, for example, generating a Fourier transform of a received signal to represent the signal in the frequency domain (e.g., to generate the spectral density of the signal). Process 500 may then include comparing the transformed signal in the frequency domain to a threshold power level and determining one or more noise frequency ranges over which the spectral power of the signal (e.g., its power in the frequency domain) exceeds the threshold power level. In these embodiments, the noise frequency ranges may reflect the frequency bands over which the received signal exhibits substantial noise artifacts. For example, process 500 may average an acceleration signal over five seconds and transform it into the frequency domain to determine that its averaged spectral power exceeds a threshold power level between the frequencies of 500 to 1,000 Hz and 2,000 to 3,000 Hz. These two ranges may reflect the noise frequency ranges of the signal (e.g., the frequencies over which the signal exhibits strong noise levels). The threshold power level may be predefined, depend on the type of signal, and/or based on a set of control variables consistent with the disclosed embodiments. In one embodiment, for instance, adaptive control device 112 may determine the threshold power level(s) for each signal based on a set of control variables 422 managed by control logic 420.

In some aspects, the noise analysis of process 500 may further include determining a minimum frequency of the one or more noise frequency ranges. In certain embodiments, this minimum frequency may reflect the lowest frequency value for which the spectral power exceeds the threshold power level. In the example above, for instance, adaptive control device 112 may determine the minimum frequency to be 500 Hz. Additionally or alternatively, process 500 may include computing a minimum frequency for each noise frequency range in the one or more noise frequency ranges. Turning again to the above example, process 500 may determine the noise frequency ranges to be associated with minimum frequencies of 500 Hz and 2,000 Hz, respectively.

Process 500 may include determining whether the one or more minimum frequencies of the one or more frequency ranges exceed(s) a threshold frequency. In some embodiments, the threshold frequency may reflect a minimum cutoff frequency for which adaptive control device 112 may apply a low-pass filter. For example, adaptive control device 112 may include a set of low-pass filters connected to each of the set of signals with varying frequency cutoffs. By way of example, adaptive control device 112 may include a set of four low-pass filters for filtering signals above 200 Hz, 400 Hz, 1,000 Hz, and 3,000 Hz. In this example, process 500 may determine the threshold frequency to be 200 Hz, as this value reflects the minimum cutoff frequency in the available low-pass filters of adaptive control device 112. In some aspects, the low-pass filters may comprise any suitable low-pass filter for conducting processes consistent with the disclosed embodiments, such as a FIR filter with 128 taps.

In some aspects, process 500 includes selecting and applying a low-pass filter under certain conditions (step 506). For example, process 500 may apply a low-pass filter when a minimum frequency of the noise frequency range(s) exceeds the determined threshold frequency. That is, process 500 may apply low-pass a noisy signal when adaptive control device 112 includes a low-pass filter capable of filtering it in its noise frequency ranges. In some embodiments, selecting a low-pass filter may comprise identifying a low-pass filter in the set of low-pass filters of adaptive control device 112 with the cutoff frequency closest to, but not exceeding, the minimum frequency of the noise frequency ranges. For example, if the noise frequency range is 500 Hz to 1,000 Hz and adaptive control device 112 includes low-pass filters with cutoff frequencies of 200 Hz, 400 Hz, 1,000 Hz, and 3,000 Hz, process 500 may identify the 400 Hz filter as the selected filter. In some aspects, process 500 may then apply the selected filter (e.g., pass the noisy signal through the selected low-pass filter) to create a filtered signal. In certain embodiments, process 500 may not apply any of the low-pass filters when the minimum frequency of a noise frequency range falls below the lowest cutoff frequency (e.g., the threshold frequency) in the set of low-pass filters. Process 500 may repeat this process for every noise frequency range for every sampled or noisy signal.

In addition to or in lieu of the low-pass filtering processes, process 500 may include determining whether residual noise artifacts exist within the set of sampled signals (step 508). In some embodiments, process 500 may identify such artifacts as noise frequency ranges having a width in the frequency domain less than a threshold noise width. By way of example, a signal in the set of signals may have a noise frequency range (e.g., a frequency range over which a noise artifact exists) of 600-640 Hz. In this example, process 500 may determine the threshold noise width to be 50 Hz (e.g., based on a parameter stored within a system of environment 100). Under these conditions, process 500 may identify this signal as warranting additional filtering, as described below. If process 500 determines that the signals do not meet such conditions, process 500 may terminate (step 510) to continue other processing consistent with the disclosed embodiments (e.g., the event detection process of FIG. 6). These determinations may be repeated for each noise frequency range for each sampled signal. In some embodiments, the threshold noise width may be predefined or generated based on, for example, a set of control variables 422 stored on adaptive control device 112. In addition, the noise frequency ranges in this process may be based on the same or different threshold power levels as the low-pass filtering processes above. For example, a noise frequency range used in step 508 may apply a lower threshold power level than one employed in the low-pass filtering processes describe above.

When process 500 identifies one or more signals exhibiting residual noise artifacts, it may select and apply a band-stop filter to those signals to attenuate them over the relevant frequencies (step 512). For example, adaptive control device 112 may include one or more band-stop filters connected to each of the set of signals with varying frequency ranges and/or attenuation strengths. These band-stop filter(s) may comprise any suitable band-stop filter for conducting processes consistent with the disclosed embodiments, such as a FIR filter with two taps. In some aspects, process 500 may determine if a band-stop filter included or configurable within adaptive control device 112 is substantially within the range of the identified residual artifacts for a particular signal (e.g., 25%, 50%, 75%, etc. of the filtered width of the band-stop filter lies within the noise frequency range). If so, process 500 may select and apply the band-stop filter to the signal (e.g., pass the signal through the band-stop filter) to attenuate it within the cutoff range. Process 500 may repeat this process for every residual noise artifact and every configurable band-stop filter. Process 500 may then end (step 510) to continue other processing consistent with the disclosed embodiments.

As described herein, any information generated or otherwise associated with process 500 may be transmitted to a remote computing system (e.g., control system 132) and/or may be used by adaptive control device 112 to update a set of operative control variables 422 (e.g., via a response signal 444 provided to control logic 420). For example, process may use information associated with determined noise frequency ranges, threshold power levels, minimum frequencies of the noise frequency ranges, selected low-pass filters, spectral densities of the sampled signals, threshold noise widths, etc., to update a set of control variables 422 and/or transmit such information to control system 132. It is intended that any variable quantity, representation, equation, relationship, etc., of process 500 can be controlled by the set of control variables, and the listing of certain parameters or their associated information is not intended to be limiting. Adaptive control device 112 may monitor for and detect such changes to the control variables 422 and may dynamically adjust processes of the disclosed embodiments accordingly.

Figure 6:
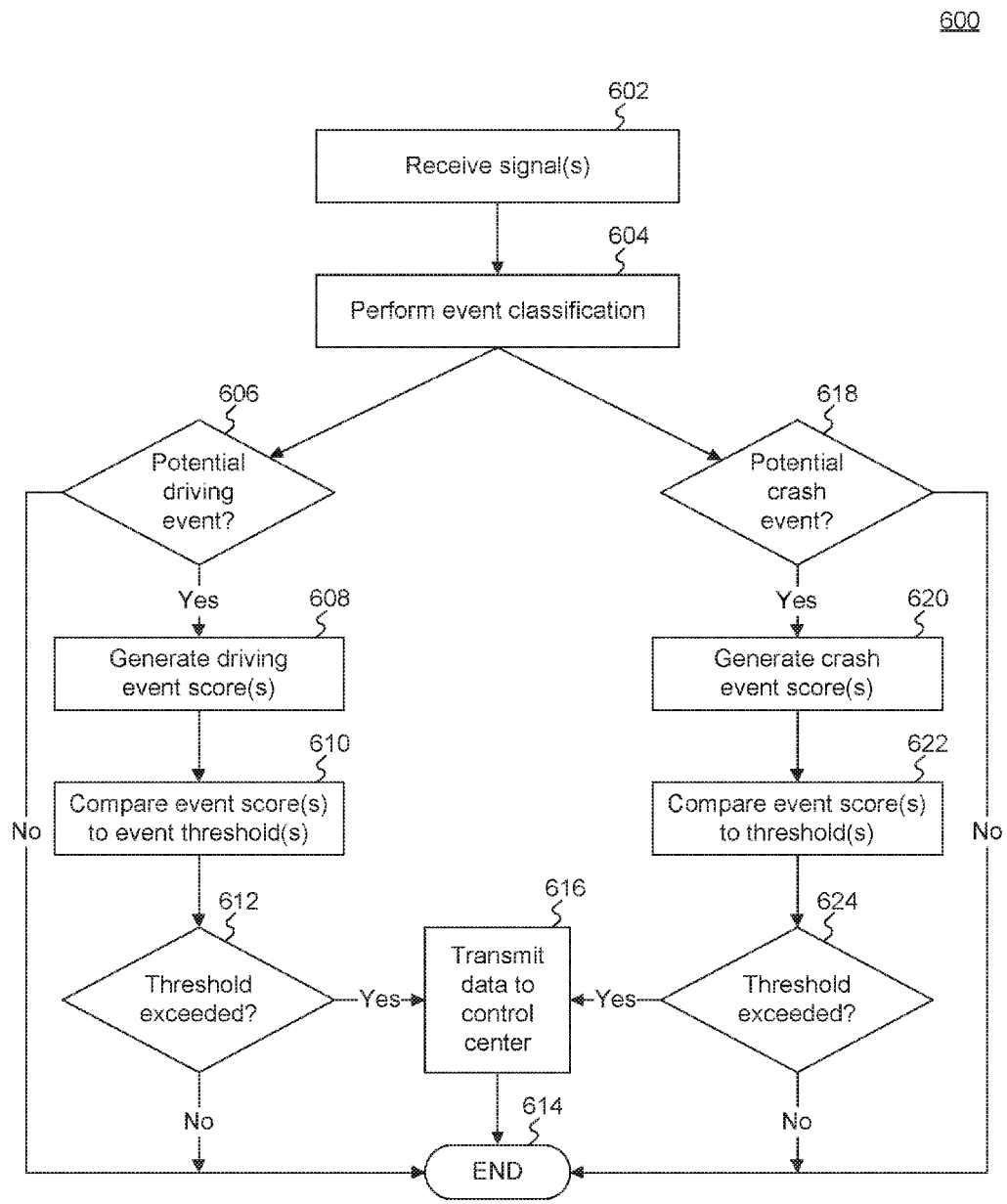
FIG. 6 depicts a flowchart for an example event detection process consistent with the disclosed embodiments.

FIG. 6 depicts a flowchart for an example event detection process 600 consistent with the disclosed embodiments. Aspects disclosed in connection with process 600 may be implemented via hardware and/or software on one or more computing systems of environment 100, such as adaptive control device 112 and control system 132. Certain aspects of process 600 may be reordered, rearranged, repeated, omitted, supplemented, modified, or integrated into additional processes in ways consistent with the disclosed embodiments. For example, embodiments described in connection with process 600 may be implemented in adaptive control device 112 to detect an occurrence of an event, such as those described in connection with step 310 of FIG. 3 or within adaptive event logic 430 of FIG. 4, etc.

In some aspects, process 600 includes receiving a set of signals associated with a set of vehicle sensors 114 (step 602). The received signals may take any form and may reflect the output of any sensor 114 or derived signal consistent with the disclosed embodiments. By way of example, process 600 may receive a set of four signals comprising a breaking, cornering, time, and acceleration signal. Any number of signals may be received in this manner. In addition, these signals may be bandwidth-filtered consistent with the embodiments described in connection with FIGS. 3-5, although such filtering is not required.

In certain embodiments, process 600 includes performing an event classification to determine whether the received signals indicate the presence of a particular class of potential event (step 604). In some aspects, identifying an event class may include determining whether the received signals correspond to or correlate with a potential driving event or potential crash event. A potential driving event may reflect specific behaviors and/or conditions warranting further analysis from adaptive control device 112 due to their association or correlation with dangerous, hazardous, or unsafe driving or conditions. A potential driving event may include any non-crash event and may correspond to any signal consistent with the disclosed embodiments. For example, potential driving events may include a potential acceleration event, braking event, cornering event, speed event, etc., or any other event corresponding to a received signal. These events may reflect, for instance, the presence of a harsh breaking event, a sudden corning event, a rapid lane change event, etc. In certain aspects, a potential crash event may indicate a likelihood that vehicle 110 is about to be or has recently been involved in a crash.

Process 600 may determine an event class of a potential event by correlating the received signals with one or more event classification models stored in memory. These event classification models may include, for example, inertial force profiles, centrifugal force profiles, speed and speed change profiles, pitch, roll, and yaw profiles, acceleration profiles, acceleration matrices, etc., associated with potential driving events and/or potential crash events. These profiles may stem from historical analyses, laboratory analyses, crash tests, control variables 422, etc., and may be provided to or stored locally on adaptive control device 112. In some aspects, process 600 may identify an event class for a potential event by determining whether a correlation measure between one or more of the received signals and the event classification model exceeds a classification threshold. The correlation measure may reflect any measure indicating a degree of fit between data and a model, such as a correlation coefficient, coefficient of determination, coefficient of multiple correlation, etc. Each event type of the potential event (e.g., a crash event, a cornering event, a speed event, etc.) may be associated with one or more event classification models with a corresponding classification threshold.

In some aspects, the event classification models and/or the classification thresholds may be selected based on a set of vehicle parameters associated with the vehicle 110. These vehicle parameters may reflect any physical or technical characteristic of vehicle 110, such as its weight, height, length, center of gravity, curb weights, turning radius, weight distribution, wheelbase, acceleration figures, redline, horsepower, torque, breaking figures, drag coefficient, vehicle type, make, model, year, etc. By way of example, adaptive control device 112 may select event classification models for vehicles of the same make or model as vehicle 110, similar weight distributions, sizes, etc., to ensure it compares vehicle 110 with similar vehicles when performing the event classification.

In some embodiments, the various parameters of the event classification process (or any routine of process 600) may be dynamically adjusted by a set of control variables 422 stored in adaptive control device 112. For example, the set of control variables 422 may define the classification threshold for each event type of a potential driving event (e.g., cornering event, speed event, acceleration event, etc.), information associated with the signal and data profiles in the event classification models, the event classes, the types of potential driving events available, etc. In addition, the information generated in the foregoing embodiments may cause changes in the set of control variables 422. For example, in one aspect, adaptive control device 112 may update the set of control variables 422 (e.g., via a response signal 448 provided to control logic 420) upon calculating a correlation between one or more signals and a potential event, determining that the correlation exceeds or falls below the classification threshold, and so on.

Process 600 may determine an event class for a potential event based on the set of received signals, the event classification models, and the classification thresholds as described above (steps 606 and 618). In some aspects, when the set of signals does not indicate the presence of either a potential driving event (step 606) or a potential crash event (step 618), process 600 may terminate (step 614) to facilitate continued processing consistent with the disclosed embodiments (e.g., monitoring sets of signals, updating control variables 422, transmitting information to control center 132, etc.).

When process 600 determines that a set of signals reflects an instance of an event class of a potential driving event (step 606), process 600 may generate or determine a representation of the event as a function of a set of event filters 432 and/or a set of signals (e.g., an event representation). This event representation may reflect a particular combination of event filters 432 for a set of signals used to determine whether the event has actually occurred. As described in connection with FIG. 4, for example, this event representation may represent the event as a logical combination of individual results from a set of event filters 432 (e.g., via combination logic 434), as a mathematical combination of individual signals subject to a single event filter, or some combination thereof. The event filters 432 and their combination (e.g., via combination logic 434) may comprise any event filter or combination consistent with the disclosed embodiments, such as those described in reference to FIG. 4 and below. In some embodiments, an event representation may be driven by a set of control variables stored on adaptive control device 112.

In some aspects, process 600 may include generating one or more event scores for the driving event (step 608). An event score may reflect a likelihood that an event or subevent has occurred. The event score may be based on one or more signals in a received set of signals. In certain aspects, an event score may be based on an event representation of the event or subevent. In one embodiment, for example, an event score S may reflect a current or time-averaged value (e.g., over some time period) of a signal x weighted by a signal weight a:

$$S = ax.$$

In some aspects, the signal weight may reflect a degree of relationship, impact, correlation, association, or importance of a signal to an event or subevent. A low signal weight may reflect that the corresponding signal does not correlate strongly to the occurrence of the event or subevent, while a high signal weight may reflect a strong correlation with the (sub)event. Similarly, a low or negative signal weight may reflect that the signal correlates with the nonoccurrence of the event (e.g., the signal inversely correlates with the event). The signal weight may take any appropriate value consistent with the disclosed embodiments, such as a number in the range [0,1], [−1,1], [1,100], and so on. In some aspects, the event score S may not be based on a signal weight (e.g., the weight for each signal is unitary or non-existent), or the event score may not incorporate a signal at all (e.g., the signal is switched off, its signal weight is zero, etc.). As another example, such as when adaptive control device 112 combines several signals into a single event filter 432, the event score S may reflect some mathematical function of the signals and their corresponding signal weight. For example, the event score S may reflect a linear combination of a set of signals $x_i$ and their corresponding signal weight $a_i$:

$$S = \sum_i a_i x_i.$$

In some aspects, process 600 may determine an event score S for every event or subevent (e.g., for every event filter 432 in the representation of the event) in this manner.

Of course, those of ordinary skill in the art will appreciate that the foregoing expressions of the event score S are merely exemplary. Any mathematical combination of signals and/or signal weights may be used to determine an event score for a particular event or subevent, given a suitable event representation permits it. For example, the event score S may be given as a product of signals and their signal weights (e.g., $S = \Pi_i a_i x_i$), as a multivariate polynomial function wherein each signal has a corresponding signal weight and power (e.g., $S = \Sigma_i a_i x_i^{b_i}$), some statistical analysis of the set of signals, any combination of these considerations, etc. In addition, the value of x may reflect any measure based on a signal, such as a time-averaged value, a measure of significance or magnitude of the signal converted from a raw value, etc. Thus, the event score S may embody any function of a set of signals (e.g., $S = f(x)$, as described in connection with FIG. 4), where the function f may comprise a single function or a composite of a set of functions operating on the set of signals.

In some embodiments, process 600 may include comparing the generated set of event scores to a corresponding set of event thresholds in the set of event filters 432 (step 610). As described above, an event threshold may reflect a value or measure defining when an event or subevent has occurred based on one or more input signals. In some embodiments, an event threshold may be based on the event class of the event (e.g., as determined in step 604), an event type of the event class (e.g., a cornering event, speed event, etc., of a general driving event), and/or a set of event factors. In some aspects, an event factor may reflect a numerical measure of interrelated information relevant to determining whether the event or subevent has occurred. The information associated with the event factors may be monitored by adaptive control device 112, received from control center 132 (e.g., reflected in one or more received boundary conditions), collected from external system 142, based on control variables 422, boundary conditions, and/or any combination of such procedures.

For example, the set of event factors may include a basic threshold factor reflecting a fixed value. In some embodiments, the basic threshold factor may be based on the event class and/or event type of the event or subevent. For example, a cornering event may have a first basic threshold factor while a speed event has a second, different basic threshold factor.

The set of event factors may also include a standard behavior factor reflecting a driver's standard or historical driving practices. The standard behavior factor may be based on information such as the driver's driving behavior (e.g., speed, position acceleration, cornering, breaking, etc.) over some moderate period of time (e.g., a number of days, weeks, or months). The standard behavior factor may also be based on the driver's claim history, general driving statistics, and one or more vehicle parameters reflecting physical or technical characteristics of vehicle 110.

The set of event factors may also include a personal status factor reflecting the driver's current driving behavior. In some aspects, the personal status factor may be based on the driver's driving behavior over a short, immediately preceding period of time (e.g., a few minutes, seconds, hours, etc.). The personal status factor may also be based on the time of day, trip information (e.g., obtained from a navigational system or as measured by adaptive control device 112), social network information and driver device information (e.g., biorhythms, sleep data, texting information, music the driver is listening to, planned routes, etc.).

The set of event factors may also include a boundary condition factor reflecting information associated with one or more boundary conditions received from control system 132. The boundary condition factor may be based on any boundary condition and the associated underlying information, such as a weather condition, road type condition, black point condition, average speed map condition, usual route condition, etc.

In some aspects, event factors may be continuously or periodically updated. In certain embodiments, each event factor may be associated with a respective update period. An update period may reflect a duration of time between successive updates of the event factor information (e.g., receipt of the information from control system 132, local generation of the information on adaptive control device 112, etc.) The update period may be based on the event factor. For example, the basic threshold factor may never update because it is fixed. In another example, the standard behavior factor may have a update period of once a week, twice a week, once a month, etc. In yet another example, the personal status factor and boundary condition factor may have a shorter update period, such as thirty or sixty seconds. In some aspects, the disclosed embodiments may dynamically adjust any other related information based on a change to the information associated with the event factors (e.g., updating the set of control variables 422, recalculating event thresholds, etc.).

In addition, the set of event factors for a particular event or subevent may depend on event class, event type, or subevent of the underlying event so that different event classes, event types, and subevents have different event factors, weigh information related to each event factor differently, have different impacts on an event threshold, etc. The set of event factors may also be based on the signals used in the comparison to the event threshold (e.g., the signals used to generate the appropriate event score). Therefore, not all of the information associated with each event factor may be implemented, queried, or received for each event, and not every event factor may be equally weighted, as described below.

Process 600 may generate an event threshold for each event filter 432 in the set of event filters to create a set of event thresholds. In some embodiments, an event threshold may be based on the event class of the event, its event type, and/or the set of event factors. In one embodiment, for example, an event threshold T for an event filter 432 may reflect the event factor f weighted by a factor weight w:

$$T = wf.$$

In some aspects, the factor weight may reflect a degree of relationship, impact, correlation, association, or importance of a factor to an event or subevent. A low factor weight may reflect that the corresponding factor does not correlate strongly to the occurrence of the event or subevent, a high factor may reflect a strong correlation, and so on. The factor weight may take any appropriate value consistent with the disclosed embodiments, such as a number in the range [0,1], [−1,1], [1,100], etc. In some aspects, the event threshold T may not be based on a factor weight (e.g., the weight for each factor is unitary), or the event threshold may not incorporate a factor at all (e.g., its factor weight is zero, etc.). As another example, the event threshold T may be based on some mathematical function of the event factors and their corresponding factor weight. For example, the event threshold T may reflect a product of the event factors $f_i$ and their corresponding factor weight $w_i$ $$T = \prod_i w_i f_i.$$

In some aspects, process 600 may determine an event threshold T for every event or subevent (e.g., for every event filter 432 in the representation of the event) in this manner.

Similar to the discussion of event scores above, those of ordinary skill in the art will appreciate that the foregoing expressions of the event threshold T are merely exemplary. Any mathematical combination of factors and/or factor weights may provide an event threshold T for a particular event or subevent, given a suitable event representation permits it. For example, the event threshold T may be given as a linear combination of event factors and their factor weights (e.g., $T=\Sigma_i w_i f_i$), as a multivariate polynomial function wherein each signal has a corresponding signal weight and power (e.g., $T=\Sigma_i w_i f_i^{v_i}$), some statistical analysis of the set of signals, any combination of these considerations, etc. Thus, the event threshold T may embody any function of a set of factors (e.g., as a single function or a composite of a set of functions), as described in connection with FIG. 4.

In some aspects, the set of factor weights may also reflect the importance, relationship, association, etc., between the component information comprising an event factor and the factor itself. Taking the personal status factor as an example, this factor may weigh a driver's immediately preceding driving history more or less heavily than social network information. The set of factor weights may reflect this weighting of the component information (e.g., each subfactor) for each factor. Thus, in some aspects, each subfactor may be associated with a respective factor weight and/or an update period, which in turn may be based on the event factor for which the subfactor serves as a component. For example, if an event factor $f_i$ is composed of subfactors $t_{ij}$, then the value of event factor $f_i$ may incorporate the weights of its subfactors, such as in the exemplary relationship $$f_i = \prod_j w_j t_{ij},$$

where $w_j$ reflects the factor weight of subfactor j of event factor i. Extending this example, process 600 may then determine the event threshold T of this event filter 432 to incorporate these subfactor weights for every event factor:

$$T = \prod_i \prod_j w_j t_{ij}.$$

In addition, each event factor may be associated with its own factor weight separate from the factor weights of its subfactors so that each event factor is also separately weighted:

$$T = \prod_i \prod_j w_{ij} t_{ij}.$$

However, as noted above, these expressions are intended for illustrative purposes only. The disclosed embodiments contemplate any type of mathematical relationship expressing an event threshold in terms of factor weights of its component subfactors (e.g., linear combinations, polynomial representations, statistical characteristics, etc.).

In some aspects, process 600 may include comparing the set of event scores to the set of event thresholds to determine if the event has occurred (step 612). Process 600 may determine that the event has occurred based on a comparison of a set of event scores (e.g., determined in step 608) with a corresponding event threshold (e.g., determined in step 610) based on the event representation of the event. In some embodiments, such as when only one event filter is applied, process 600 may determine the occurrence of an event when the event score exceeds the event threshold, S>T. In other embodiments, such as when several event filters 432 are applied (e.g., as defined in the event representation), process 600 may determine when an event has occurred based on a logical combination of the results of each comparison between the event scores and the event thresholds (e.g., via combination logic 434 and the event representation). This logical combination may employ any permutation of logical operators such as AND, OR, XOR, and/or NOT reflecting the event representation in logical terms, as described in reference to FIG. 4.

By way of extended example, suppose that adaptive control device 112 samples two signals $x_1$ and $x_2$ (e.g., pitch and yaw) to determine whether an event E has occurred. Suppose that these signals are associated with signal weights $a_1$ and $a_2$. Suppose further that an event threshold for E comprises the four factors enumerated above, abbreviated BTF, SBF, PSF, BCF, each made up of a number of subfactors, and each factor weight is unitary (e.g., there are no weight factors). Finally, suppose that a generated event representation uses the expressions above for an event score (e.g., a linear combination) and an event threshold (e.g., a product of event factors). Any or all of these parameters may be based on (and controlled by) control variables 422 stored in adaptive control device 112. In a first example under these conditions, adaptive control device 112 may determine that E occurs when $$S_E = a_1 x_1 + a_2 x_2 > BTF \cdot SBF \cdot PSF \cdot BCF = T_E.$$

In a second example under these conditions, suppose instead that the event representation reflects that both signals are subjected to their own event filter 432 and that E occurs when both event filters for the subevents return true. Adaptive control device 112 may then determine E occurs when $$E = SR_1 \land SR_2 = (a_1 x_1 > BTF_1 \cdot SBF_1 \cdot PSF_1 \cdot BCF_1) \land (a_2 x_2 > BTF_2 \cdot SBF_2 \cdot PSF_2 \cdot BCF_2).$$

As explained above, such expressions are intended to be illustrative and do not limit the disclosed embodiments to particular expressions.

When process 600 determines that an event has not occurred based on the set of event scores and the set of event thresholds, process 600 may terminate (step 614) to continue further processing consistent with the disclosed embodiments (e.g., updating control variables 422, transmitting information to control center 132, etc.). When process 600 determines that an event has occurred, process 600 may transmit event data to a remote system such as control system 132 (step 616). The event data may take any form and any include any information consistent with the disclosed embodiments, such as those described in connection with step 312 of FIG. 3. For example, the event data may include a notification that an event has occurred so that control system 132 may receive this information and conduct additional processing (e.g., as described in reference to FIG. 8).

When process 600 determines that a set of signals reflects an instance of an event class of a potential crash event (step 618), process 600 may perform similar operations to those described above. For example, process 600 generate or determine an event representation representing the crash event as a particular combination of event filters 432 for a set of signals. Process 600 may also generate a set of event scores for the crash event based in part on the event representation (e.g., based on the arrangement of event filters 432) (step 620). Process 600 may then generate a set of event thresholds and compare each event score in the set of event scores to a corresponding event threshold (step 622).

In some aspects, the event thresholds for crash event may be determined in a manner similar to that of driving events. For example, the set of event thresholds may be based an event class of the event (e.g., a crash event), an event type (e.g., a type of crash), and/or a set of event factors. The set of event factors may be based on the event class and/or event type, in addition to other information consistent with the disclosed embodiments. The event factors for a crash event may be the same or different than those of a driving event. In one embodiment, for example, a crash event may be associated with different event factors from a driving event. In addition, each factor in the set of event factors may also be associated with a respective update period, and may be maintained in ways similar to those described above. The set of event factors may also be associated with a set of factor weights pertaining to the event factors and/or their subfactors consistent with the foregoing embodiments.

For example, the set of event factors may include a device factor reflecting information associated with the installation of adaptive control device 112 and its relationship to vehicle 110. In some aspects, for instance, the device factor may include information associated with device type associated with adaptive control device 112, a position and quality of installation of adaptive control device 112 within vehicle 110, and/or one or more vehicle parameters such as a vehicle type.

The set of event factors may also include a relative threshold factor reflecting an average behavior of all vehicles within a certain fleet class of vehicle 110. In some embodiments, the fleet class of vehicle 110 may include similar or all cars located within the same city, state, etc. of vehicle 110. Additionally or alternatively, the fleet class of vehicle 110 may include some or all vehicles for all drivers having a similar driving profile (e.g., based on monitored or stored driving behavior), etc.

The set of event factors may include a current hazard factor associated with vehicle 110. In some aspects, the current hazard factor may be based on a hazard index currently associated with vehicle 110, such as a hazard index received from control center 132 or generated with adaptive control device 112 and stored in memory. As described herein, the hazard index may reflect a degree of exposure to danger or unsafe driving associated with vehicle 110. The current hazard factor and/or the hazard index may be based on, for instance, detecting that a dangerous event has occurred such as a harsh breaking event, a sudden corning event, a fast lane change event, or other type of event consistent with preimpact driving behaviors.

The set of event factors may include a weather factor reflecting current weather conditions around vehicle 110. In some embodiments, this factor may be based on information contained in a weather condition received from control center 132 and/or environmental conditions sensed with sensors 114, such as temperature, humidity, moisture levels, etc.

The set of event factors may also include a service level factor reflecting information associated with a service-level agreement with a driver of vehicle 110. In some aspects, the service level factor may be based on the amount and/or type of information the driver has authorized adaptive control device 112 and/or control system 132 to collect, monitor, detect, process, or retrieve.

Using these event factors and/or those described above in reference to driving events, process 600 may generate a set of event thresholds using the expressions and considerations explained above. In some embodiments, process 600 may generate an event threshold for each event filter 432 in the set of event filters so that it may compare the set of event scores to the set of event thresholds (step 622). For example, process 600 may calculate an event threshold T for each event filter 432 based on a set of factor weights $w_i$ (e.g., governing the factors or their component subfactors) and each event factor, such as the exemplary relationship $T=\Pi_i w_i f_i$. Those of ordinary skill in the art will appreciate modifications to this exemplary expression consistent with the disclosed embodiments.

Process 600 may include comparing the set of event scores to the set of event thresholds to determine if the event has occurred (step 624) in a manner similar to the above processes, such as those described in connection with step 612. For example, process 600 may determine that the event has occurred based on a comparison on the set of event scores (e.g., from step 620) with a corresponding event threshold (e.g., from step 622). This determination may be based on, for example, an event representation reflecting a mathematical and/or logical combination of event filters 432 and/or signals symbolizing the event. As described above, process 600 may then terminate (step 614) when the event is not detected to continue processing consistent with the disclosed embodiments. When process 600 detects an event, process 600 may transmit event data to control system 132, as disclosed herein.

The various parameters of process 600 may be controlled by a set of control variables 422 stored on adaptive control device 112. In one example, the set of control variables 422 may govern processes associated with existing event classes (e.g., the characteristics and types of available classes), event types (e.g., the available types of driving events such as cornering events, speed events, etc.), event classification models (e.g., the model signal profiles, how the models are applied, how an appropriate model is selected for a vehicle based on vehicle parameters), correlation measures (e.g., how the measure is calculated given a set of signals or profiles), and/or classification thresholds (e.g., the value of the threshold, how each threshold varies according to event class/type, etc.), etc. In another example, the set of control variables 422 may control processes associated with the set of event scores (e.g., how an event score is calculated as a function of a set of signals), event thresholds (e.g., how an event threshold is calculated as a function of event factors), event factors (e.g., the subfactors comprising each factor, the set of factors used to compute the event threshold), signal weights and factor weights (e.g., the values of the various weights, whether a factor weight applies to subfactors), and the like. Any variable quantity, representation, equation, relationship, etc., of process 600 can be controlled by the set of control variables 422, and the listing of certain parameters or their associated information above is not intended to be limiting.

In certain aspects, the generation or determination of any parameter described above (e.g., detecting an event, calculating an event threshold or event score, determining an event representation, etc.) may cause adaptive control device 112 to change the set of operative control variables 422 (e.g., via response signal 448). For example, in one embodiment, adaptive control device 112 may update a set of control variables 422 upon detecting the occurrence or nonoccurrence of an event. Changes to the set of control variables may cause adaptive control device 112 to dynamically adjust the disclosed embodiments (e.g., by adjusting a parameter disclosed in connection with FIGS. 3-8) based on the detected changes. For example, adaptive control device 112 may adjust any of the parameters above in response to a change in the operative set of control variables. Adaptive control device 112 may automatically and continually monitor for changes to the set of control variables 422 so that it may dynamically adjust parameters on the disclosed embodiments in response to the detected change. In addition, any aspect of the foregoing parameters or their associated information may be transmitted to control center 132 to conduct further processing consistent with the disclosed embodiments.

Figure 7:
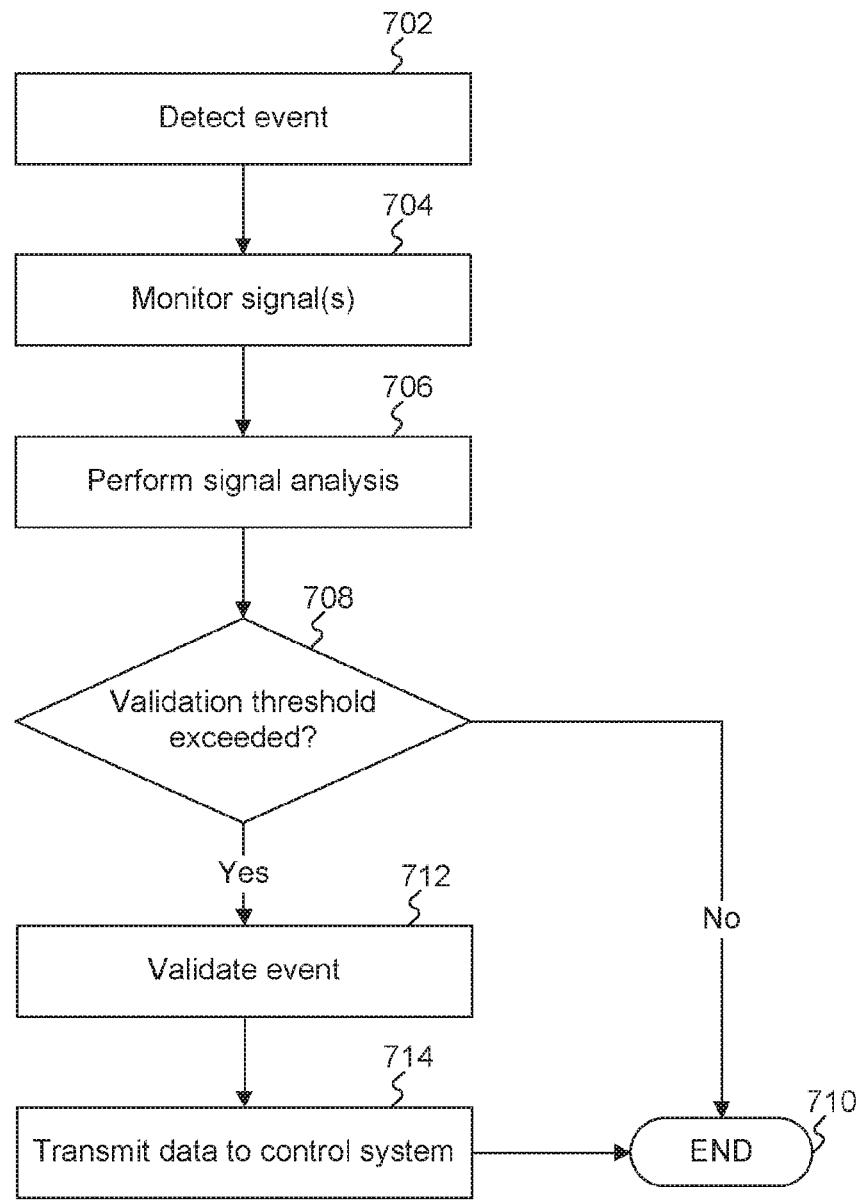
FIG. 7 depicts a flowchart for an example event validation process consistent with the disclosed embodiments.

FIG. 7 depicts a flowchart for an example event validation process 700 consistent with the disclosed embodiments. Aspects disclosed in connection with process 700 may be implemented via hardware and/or software on one or more computing systems of environment 100, such as adaptive control device 112 and control system 132. Certain aspects of process 700 may be reordered, rearranged, repeated, omitted, supplemented, modified, or integrated into additional processes in ways consistent with the disclosed embodiments. For example, embodiments described in connection with process 700 may be implemented in adaptive control device 112 to validate an occurrence of a detected event, such as those described in connection with the post-processing step 312 of FIG. 3.

Process 700 may include detecting an event consistent with the disclosed embodiments (step 702). In certain aspects, this event detection may include aspects of the event detection processes disclosed in reference to FIGS. 3, 4, and 6. For example, process 700 may include detecting a crash event with adaptive control device 112 using the processes disclosed herein. In some embodiments, process 700 may occur only upon the detection of certain event classes (e.g., crash events) or certain event types. In one embodiment, for instance, process 700 may occur only in response to detecting a crash event.

Process 700 may include monitoring a set of signals with adaptive control device 112 in response to detecting the event (step 704). The set of signals may be fixed or may depend on the event class of the detected event, its event type, or a set of control variables 422, etc. For example, in one embodiment, process 700 may measure signals such as those associated with speed, longitudinal acceleration, yaw, and distance. Process 700 may monitor the set of signals for a period of time equal to an observation period (e.g., fifteen seconds, thirty seconds, one minute, etc.) after detecting that the event has occurred. In certain aspects, the observation period may be based on an event class, event type, the set of signals monitored, a set of operative control variables 422, etc. In other aspects, the observation period may remain fixed.

Process 700 may perform a signal analysis of the monitored signals to validate the event (step 706). Performing a signal analysis of the monitored signals may include generating a validation measure associated with the set of monitored signals and comparing it to a validation threshold. In some embodiments, a validation measure may reflect a likelihood or a degree of certainty that the detected event truly occurred. In some aspects, a validation measure may be based on a set of validation weights reflecting a degree of relationship or correlation between a signal and the detected event as a function of a set of validation parameters. The set of validation parameters may represent a basis for the validation weights so that any validation weight may be constructed as an expression of the validation parameters. For example, the set of validation parameters may include a speed trend before the detected event (e.g., over some period of time), a type of road on which vehicle 110 is traveling, a time of day, and a weather condition.

In some aspects, process 700 may determine a validation measure as a function of the set of monitored signals and validation weights. This expression may take any appropriate mathematical or statistical form consistent with the disclosed embodiments. For example, given a set of monitored signals x (e.g., speed, longitudinal acceleration, yaw, and distance, based on an event class), process 700 may determine a validation measure V using a set of validation parameters v:

$$V = \sum_i f_i(v) x_i$$

where $f_i(v)$ reflects a validation weight for signal i expressed as a function f of the validation parameters v. As with the expressions of event scores and event thresholds, the relation above is intended to be exemplary. Those of ordinary skill in the art will appreciate alternate expressions for the validation measure (e.g., as a single or composite function) based on a set of input signals and validation parameters.

Process 700 may include comparing the determined validation measure to a validation threshold to validate the event (step 708). In some embodiments, a validation threshold reflects a minimum likelihood or degree of certainty necessary to validate that a detected event occurred. The validation threshold may be fixed or based on other considerations such as an event class or event type of the detected event, the signals monitored, the validation parameters used, etc. When process 700 determines that the validation measure does not exceed the validation threshold, the event may not be validated and process 700 may terminate to facilitate further processing (step 710). Alternatively, when process 700 determines that the validation measure exceeds the validation threshold, process 700 validates the event (step 712). In some embodiments, such processing may include storing information associated such validation in memory and conduct further processing, such as updating a set of operative control variables 422 based on the validation. In addition, process 700 may transmit validation data to control system 132 (step 714). In certain aspects, validation data may take a form similar to event data and may include any information associated with the validation routines of process 700. For example, validation data any include an indication that a detected event was validated, a value for the validation measure or validation threshold, the set of signals monitored, the set of event parameters used, etc. The validation data may take any appropriate form consistent with the disclosed embodiments such as a signal, a computer file, etc.

The various parameters of process 700 may be controlled by a set of control variables 422 stored on adaptive control device 112. In one example, the set of control variables 422 may govern processes associated with monitoring the signals (e.g., determining observation periods, the set of signals to monitor, etc.) and/or performing the signal analysis (e.g., defining the validation threshold, defining the validation parameters and validation weights, defining how to compute a validation threshold given a set of validation parameters and a set of signals, etc.). Any variable quantity, representation, equation, relationship, etc., of process 700 can be controlled by the set of control variables, and the listing of certain parameters or their associated information above is not intended to be limiting. Moreover, the generation or determination of any parameter described in reference to process 700 may cause a change in the set of operative control variables 422 (e.g., via a response signal 448). For example, adaptive control device 112 may update a set control variables upon validating the occurrence of a detected event. Changes to the set of control variables 422 may cause adaptive control device 112 to dynamically adjust the disclosed embodiments (e.g., by adjusting a parameter disclosed in connection with FIGS. 3-8) based on the detected changes. For example, adaptive control device 112 may adjust any of the parameters above in response to a change in the operative set of control variables. Adaptive control device 112 may automatically and continually monitor for changes to the set of control variables 422 so that it may dynamically adjust parameters on the disclosed embodiments in response to the detected change. In addition, any aspect of the foregoing data or parameters and their associated information may be transmitted to an external system (e.g., control system 132) to conduct further processing consistent with the disclosed embodiments.

Figure 8:
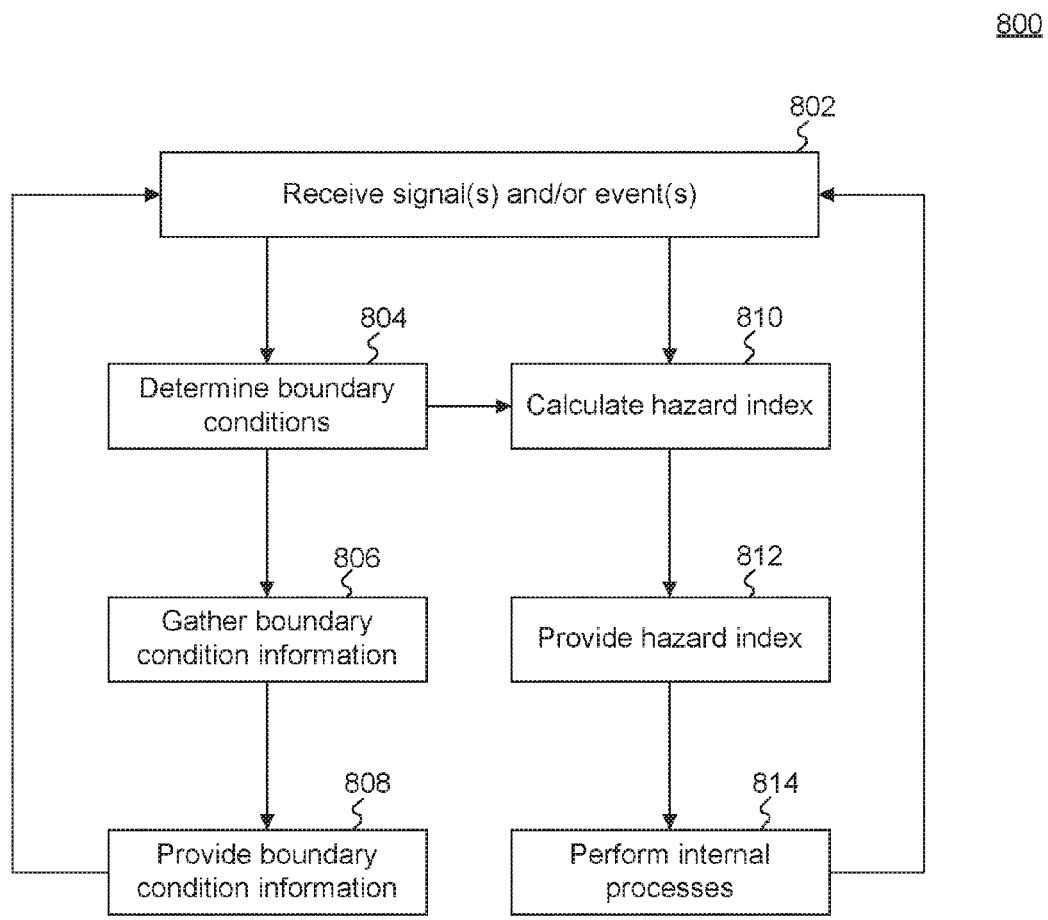
FIG. 8 depicts a flowchart for an example process for generating boundary conditions and hazard indices consistent with the disclosed embodiments.

FIG. 8 depicts a flowchart for an example process 800 for generating boundary conditions and hazard indices consistent with the disclosed embodiments. Aspects disclosed in connection with process 800 may be implemented via hardware and/or software on one or more computing systems of environment 100, such as adaptive control device 112 and control system 132. Certain aspects of process 800 may be reordered, rearranged, repeated, omitted, supplemented, modified, or integrated into additional processes in ways consistent with the disclosed embodiments. For example, embodiments described in connection with process 800 may be implemented in control system 132 to sets of boundary conditions and hazard indices, such as those described in connection with the step 302 of FIG. 3.

In certain aspects, process 800 may include receiving a set of signals or information associated with a detected event from adaptive control device 112 (step 802). In some embodiments, process 800 may also receive information and parameters associated with other processes, such as the bandwidth filtering process, event detection process, and/or validation process, among others. For example, control system 132 may receive information associated with an applied low-pass filter, signals received via adaptive control device 112, a event threshold, a validation measure, etc. Such received information may include any information associated with the disclosed embodiments and may arrive (e.g., may be transmitted by adaptive control device 112) at any step of the foregoing processes.

Process 800 may include determining a set of boundary conditions to provide to adaptive control device 112 based on the received information (step 804). In some aspects, determining the set of boundary conditions may comprise identifying a set of possible events implicated by the received signals and determining one or more boundary conditions pertinent to the set of possible events. For example, control system 132 may receive a speed signal from adaptive control device 112 indicating that vehicle 110 is traveling at a high rate of speed. In response, control system 132 may determine that high rates of speed are, for example, often associated with speed events, crash events, braking events, etc. Control system 132 may further determine that the boundary conditions often pertinent to these events include, for example a road type condition (e.g., to account for highways), a weather condition (e.g., to ensure driver is not speeding in the rain), an average speed map condition (e.g., to gauge or compare the driver to those in her vicinity), and/or a comparison between the personal status factor and the standard behavior factor (e.g., to compare the driver against his typical habits). These identified boundary conditions may comprise the set of determined boundary conditions. Of course, other permutations of boundary conditions are possible, and the above example is provided for illustration purposes only. In some aspects, control system 132 may store in memory an event mapping that maps observed trends, profiles, or signatures in a set of signals to a set of potential events. In addition, control system 132 may store a boundary condition mapping that maps a set of potential events to a set of pertinent boundary conditions. In this manner, control system 132 may determine the pertinent boundary conditions by comparing the values of the set of sensors with the event mapping to identify potential events, and in turn identifying a set of pertinent boundary conditions based on the identified potential events using the boundary condition mapping.

Process 800 may include gathering, collecting, and generating information associated with the set of identified boundary conditions (step 806). This information may reflect data relevant to the identified boundary conditions, and may depend on the set of boundary conditions identified. For example, if process 800 identifies a weather condition or a social network condition, process 800 may collect or generate information associated with the weather conditions surrounding vehicle 110 (e.g., current or expected based on a predicted route, as described above), or may collect information from one or more social networking sites associated with the driver. Process 800 may collect other types of information, depending on the set of identified boundary conditions. The information collected or generated with process 800 may be created locally (e.g., on control system 132), or may be obtained from remote systems (e.g., external system 142). For example, if process 800 has identified social networking or device conditions, process 800 may obtain the required information from several external systems 142 reflecting the driver's devices (e.g., a smartphone, wearable devices like a smartwatch, navigational systems, etc.) and servers associated with one or more social networking sites. Process 800 may include obtaining data from external systems 142 storing traffic information, weather information, etc. In other example, process 800 may occur locally on control system 132, such as when the control system generates information associated with the driver's historical driving conditions (e.g., based on monitored signals from adaptive control device 112), etc. The information collected or generated in this manner may include any information consistent with the disclosed boundary conditions, such as weather information, vehicle speed maps, traffic conditions, driver statistics, road information, or other information described in connection with FIG. 3.

Process 800 may also include providing the boundary conditions and/or the associated information to adaptive control device 112 for further processing (step 808). Process 800 may provide the boundary conditions and other information over any suitable communications network (e.g., communications network 120). The provided boundary conditions and other information may take any suitable form, such as a signal, a computer file, etc. In some embodiments, adaptive control device 112 may receive the boundary conditions and associated information from control system 132 to conduct additional processes described herein. For example, in some aspects, adaptive control device 112 may update a set of control variables 422 based on the received information (e.g., by updating a set of external variables 426 to account for the new set of boundary conditions). Adaptive control device 112 may also store information associated with the new set of boundary conditions, for example, to determine additional changes to control variables 422, or to use in the disclosed processes such as event detection, etc. In this manner, adaptive control device 112 may use the information received from control center 132 to drive changes in its internal process and dynamically adjust how it collects and processes data. Process 800 may continue to monitor for received signals or other information from adaptive control device 112 (e.g., based on the updated boundary conditions) to begin the process anew (step 802).

In some embodiments, process 800 may include generating a hazard index associated with the driver or vehicle 110 (step 810). This hazard index may be based on information received from adaptive control device 112 (step 802) and/or any identified boundary conditions previously generated or newly determined (e.g., step 804). In some aspects, process 800 may determine the hazard index based on information stored or generated on control system 132 and/or information monitored by adaptive control device 112. Process 800 may determine a value of the hazard index using formulae, weights, and parameters consistent with those disclosed above (e.g., weight averages, products, functions of various parameters, etc.). In one embodiment, process 800 may determine the value of the hazard index based on a driver's driving behavior. Process 800 may identify a driver's behavior based on signals or other information received from adaptive control device 112 (e.g., speed, acceleration, cornering, breaking, and/or position signals; detecting driving events such as speeding or cornering events, etc.), as well information stored on control system 132 (e.g., a driver's historical driving behavior and statistics).

In certain embodiments, the hazard index may also be based on the driver's attention. Process 800 may determine a measure of the driver's attention based on information associated with current boundary conditions. For example, process 800 may measure a driver's attention based on data such as a device condition (e.g., indicating the driver is sending a text message while driving), average speed map condition (e.g., indicating the driver is driving at a speed significantly different from other drivers in her proximity for a given time period), and other such boundary conditions. Additionally or alternatively, process 800 may measure a driver's attention based on signals or information received from adaptive control device 112, such as the presence of several corning events or acceleration events within a short time window.

In certain aspects, the hazard index may also be based on information associated with a vehicle's environment. Process 800 may measure environmental information using data received from adaptive control device 112 (e.g., via temperature, humidity, moisture levels), as well as identified boundary conditions and associated data (e.g., a weather condition, including weather information pulled from external system 142).

Process 800 may include providing the generated hazard index to adaptive control device 112 to conduct further processing (step 812). Process 800 may provide the hazard index via any appropriate channel or communications network. In some aspects, adaptive control device 112 may receive the hazard index and update its internal processes accordingly. For example, adaptive control device 112 may change a set of operable control variables 422 based on a new value of the hazard index (e.g., replacing or averaged into an old index) to reflect an updated exposure to danger. In certain aspects, for instance, the various event thresholds and/or validation thresholds may be inversely proportional to a received hazard index (e.g., to detect more events in a more dangerous environment), sampling rates and/or signal weights may be directly proportional to the hazard index (e.g., to sample signals more frequently during times of danger), certain signals, factors, and/or their associated weights may become more or less relevant, and the like. Adaptive control device 112 may compare a new hazard index to an old one, determine the necessary changes to make in its internal processes, and modify the set of operative control variables 422 to effectuate these changes (e.g., by changing a set of external control variables 426).

Process 800 may also include performing internal processing based on the updated hazard index and/or other information associated with process 800 (step 814). In some aspects, for instance, process 800 may include providing a notification to a driver based on a newly determined hazard index and/or boundary condition information. The notification may include information associated with the hazard index, such as an indication that the driver is driving is a more dangerous or safer manner compared to a previously determined hazard index, historical averages of hazard indices for the driver or similarly situated drivers, etc. The notification may also include information associated with the set of boundary conditions, such as an indication of the driver's driving habits or behaviors in connection with one or more boundary conditions. For example, the notification may indicate that the driver is driving too quickly during rainy weather conditions, that the driver has fewer cornering or acceleration events than those similarly situated to her by location/vehicle type, or any other type of indication. In this manner, the notification may include kind of driving analysis consistent with the disclosed embodiments and combinations thereof. This notification may comprise an e-mail, text message, automated voice message, pop notification on a mobile device display, or other similar format. Process 800 may continue to monitor for signals or other information from adaptive control device 112 after conducting its internal processes, beginning the process anew.

Additionally or alternatively, process 800 may include conducting internal processes associated with a control center 130 using control system 132. For example, in one embodiment, process 800 may include updating one or more insurance policies associated with vehicle 110 based on the signals received from adaptive control device 112, generated hazard indices, and detected events (or lack thereof). In some aspects, for instance, lower hazard indices, an absence or infrequency of driving or crash events, and signals correlating strongly with standard driving behaviors may indicate that a driver of vehicle 110 is generally a safe driver. Process 800 may thus include determining a change to an existing insurance policy associated with vehicle 110 based on the signals received from adaptive control device 112, generated hazard indices, identified boundary conditions and their associated information, and the results of event detections and event validations. Such changes may include, for example, an updated insurance premium, a rebate, lower deductibles, additional coverages, etc. Process 800 may further include updating the policy based on the determined change and/or providing a notification to a driver or a determined policyholder associated with the policy including information associated with a determined change (e.g., that the policyholder is eligible for an updated premium). The notification may take a similar form to those described above.

As should be apparent from the foregoing embodiments, aspects of the disclosed embodiments enable adaptive control device 112 to dynamically adjust its collected signals, parameters, thresholds, and functions upon detecting changes to a set of control variables 422 stored in memory. As described herein, adaptive control device 112 may continually or periodically monitor the operative set of control variables to determine if a change has occurred and may dynamically adjust its processes accordingly. In addition, adaptive control device 112 may also determine one or more changes to make to a set of control variables 422 based on the foregoing processes (e.g., those described in connection with FIGS. 3-8), and update the control variables itself. Adaptive control device 112 may determine the changes to the control variables 422 and their corresponding effects on the internal processes (e.g., thresholds, functions, weights, signals sampled, etc.) based on the nature of the processed information.

For example, when adaptive control device 112 receives a hazard index from control center 132, adaptive control device 112 may update a set of external control variables 426 stored in memory. Adaptive control device 112 may then determine one or more changes to apply to aspects of the foregoing embodiments based on the new hazard index, and dynamically adjust its processes accordingly (e.g., via a control signal 442 or 446). The nature of the determined changes may be based on the nature of the new hazard index. As described above, for example, a higher hazard index indicates more dangerous driving. In some aspects, adaptive control device 112 may therefore change the set of sampled signals to favor driving-based signals (e.g., speed, corning, and acceleration signals over temperature and humidity signals, etc.). Adaptive control device 112 may also change (e.g., increase) sampling rates of these or other signals so that it collects additional and more accurate data. Adaptive control device 112 may also decrease the sampling rates of other, less important signals during times of elevated hazard indices. Further, adaptive control device 112 may modify its event detection logic to increase its sensitivity, such as decreasing event thresholds (e.g., manually, by modifying event factors and event weights to induce such a change, by modifying an event representation to adjust a mathematical representation of the threshold, etc.), increasing event scores (e.g., manually or modifying signals and their signal weights in a similar manner as changing the event thresholds), and so on. In addition, adaptive control device 112 may modify its validation processes in a similar fashion, such as decreasing validation thresholds, increasing validation measures, implementing changes to the underlying parameters and functions to induce these changes (e.g., by increasing validation weights, selecting new signals or validation parameters, etc.). Adaptive control device 112 may therefore determine how to dynamically adjust any input, parameter, or process discussed herein in response to the new control parameters 422 caused by receipt of the new hazard index. Moreover, adaptive control device 112 may determine how to dynamically adjust any such feature based on a change to a set of control parameters induced by processed information (e.g., as received from control system 132 or as generated within adaptive control device 112).

As another example, adaptive control device 112 may receive boundary conditions from control center 132 and their associated information. Adaptive control device 112 may determine how to modify the set of control variables 422 (e.g., the set of external control variables 426 in particular) and the corresponding adjustments to the foregoing processes based on the nature of the boundary conditions and the accompanying data. In one example, adaptive control device 112 may receive a weather condition when no such condition was previously established. Adaptive control device 112 may update the control variables 422 and dynamically adjust signals and sampling rates from sensors 114 to collect environmental information (e.g., temperature, moisture levels, barometric pressure, etc.). Adaptive control device 112 may also update its event detection and validation processes as outlined above (e.g., by modifying event thresholds, validation thresholds and/or their various components such as signal weights, event factors, etc.) to incorporate weather considerations into the events. In one embodiment, for instance, adaptive control device 112 may decrease event thresholds for rainy weather (e.g., because it is more hazardous), and increase the event thresholds for mild or sunny weather. Adaptive control device 112 may also sample certain types of signals more frequently (e.g., speed, cornering, breaking, etc.) in rainy conditions than in sunny conditions. In a similar fashion, adaptive control device may dynamically adjust the signals, sampling rates, thresholds, etc. of the foregoing embodiments in response to traffic conditions (e.g., due to a higher likelihood of an accident in higher congestion levels), road information (e.g., sampling signals less frequently on straighter roads), and any other boundary condition information. These kinds of changes may be applied to any variable process disclosed herein, and the changes may be based on the nature of the boundary condition information.

In a final example, adaptive control device 112 may also determine how to update a set of control variables based on internal processes. As one example, adaptive control device 112 may determine how to change a set of control variables 422 (e.g., internal variables 424) and the corresponding adjustments to the foregoing processes based on the nature of a detected event. By way of example, adaptive control device 112 may detect a speeding, acceleration, or cornering event and determine that such an event typically reflects a more dangerous or unsafe driving behavior. In response, adaptive control device 112 may update the set of control variables 422 and may dynamically adjust inputs, parameters, and processes of the foregoing embodiments accordingly (e.g., via control signal 442). For example, adaptive control device 112 may adjust the set of signals sampled (e.g., to favor driving-based signals such as speed and acceleration) and/or their sampling rates (e.g., to sample driving-based signals more frequently and environment-based samples less frequently). In addition, adaptive control device 112 may reduce event thresholds or validation thresholds in response to the detected driving event or increase event scores and validation measures, as described above, to increase a sensitivity to certain driving behaviors. Moreover, adaptive control device 112 may make the inverse changes in response to an absence of such events (e.g., by increasing event thresholds, reducing sampling rates, etc.). The disclosed embodiments contemplate making any such change in response to any information or data generated in the disclosed embodiments. Further, these changes may be applied to any variable process or parameter disclosed herein. The nature of the adjustments and the affected inputs, processes, and parameters will depend on the nature of the information generated, depending on the actual driving behaviors and environmental conditions associated with vehicle 110.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a device system or existing communications software.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including reordering steps and/or inserting or deleting steps. In addition, any parameter, condition, information, etc., described herein may reflect historical, current, or expected values of that parameter, condition, or information.

The features and advantages of the disclosure are apparent from the detailed specification, and thus, it is intended that the appended claims cover all systems and methods, which fall within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other embodiments will be apparent to those skilled in the art from consideration of the specification and practice of the embodiments disclosed herein. It is intended that the specification and examples be considered as example only, with a true scope and spirit of the disclosed embodiments being indicated by the following claims.

What is claimed:
1. A system for dynamically controlling sensor-based data acquisition in vehicles, comprising:
  a memory storing a set of instructions; and
  one or more processors configured to execute the set instructions to perform one or more operations, the operations comprising:

receiving a set of signals associated with a set of sensors in a vehicle, wherein the set of signals is associated with a set of sampling rates,
applying a set of bandwidth filters to the set of signals to create a set of filtered signals, and
detecting an occurrence of an event by comparing an event score based on the set of filtered signals with an event threshold, wherein:
at least one of the set of signals, the set of sampling rates, the set of bandwidth filters, the event score, or the event threshold is dynamically adjusted based on a change to a set of control variables, wherein the set of control variables is changed in response to detecting occurrences of subsequent events, wherein each change to the set of control variables causes a modification to at least one of the set of signals, the set of sampling rates, the set of bandwidth filters, the event score, or the event threshold;
wherein the set of control signals comprises:
a set of local control variables based on the set of signals; and
a set of external control variables based on a hazard index received from the control system,
the event threshold is inversely proportional to the hazard index,
the hazard index is based on the event data and a set of boundary conditions reflecting conditions external to the vehicle, and
the set of boundary conditions includes at least two of a weather condition, a traffic condition, a road type condition, or an average speed map condition.

2. The system of claim 1, wherein dynamically adjusting the set of signals further comprises switching off a selected signal in the set of signals or switching on a new signal not included in the set of signals.

3. The system of claim 1, wherein applying a set of bandwidth filters further comprises:
determining a noise frequency range for a noisy signal in the set of signals;
determining whether a minimum frequency of the noise frequency range exceeds a threshold frequency; and
applying a low-pass filter to the noisy signal when the minimum frequency exceeds the threshold frequency, wherein the low-pass filter has a cutoff frequency less than the minimum frequency.

4. The system of claim 3, wherein applying the set of bandwidth filters further comprises applying a band-stop filter to the noisy signal when a width of the noise frequency range is less than a threshold width, the band-stop filter attenuating the noisy signal within the noise frequency range in the frequency domain.

5. The system of claim 4, wherein determining the noise frequency range and width of the noise frequency range causes the change to the set of control variables, and wherein dynamically adjusting the set of bandwidth filters further comprises applying the low-pass filter or the band-stop filter to the noisy signal.

6. The system of claim 1, wherein the operations further include determining an event class associated with the event based on the set of filtered signals and a set of vehicle parameters reflecting physical characteristics of the vehicle, wherein the event threshold is based on the event class and a set of event factors based on the event class, and wherein determining the event class causes the change to the set of control variables.

7. The system of claim 6, wherein:
the set of signals is associated with a set of signal weights based on the control variables;
the event score is further based on the set of signal weights; and
dynamically adjusting the event score further comprises modifying the set of signals or the set of signal weights.

8. The system of claim 6, wherein:
the set of event factors is associated with a set of factor weights based on the control variables;
the event threshold is further based on the set of factor weights; and
dynamically adjusting the event threshold further comprises modifying the event class, the event factors, or the factor weights.

9. The system of claim 1, wherein the operations further comprise outputting event data when the event score exceeds the event threshold for the event and each of the subsequent events.

10. A method for dynamically controlling sensor-based data acquisition in vehicles, comprising the following operations performed via one or more processors associated with a device within the vehicle:
receiving a set of signals associated with a set of sensors in a vehicle, wherein the set of signals is associated with a set of sampling rates;
applying a set of bandwidth filters to the set of signals to create a set of filtered signals; and
detecting an occurrence of an event by comparing an event score based on the set of filtered signals with an event threshold, wherein:
at least one of the set of signals, the set of sampling rates, the set of bandwidth filters, the event score, or the event threshold is dynamically adjusted based on a change to a set of control variables, the set of control variables is changed in response to detecting occurrences of subsequent events, wherein each change to the set of control variables causes a modification to at least one of the set of signals, the set of sampling rates, the set of bandwidth filters, the event score, or the event threshold;
a set of local control variables based on the set of signals; and
a set of external control variables based on a hazard index received from the control system,
the event threshold is inversely proportional to the hazard index,
the hazard index is based on the event data and a set of boundary conditions reflecting conditions external to the vehicle, and
the set of boundary conditions includes at least two of a weather condition, a traffic condition, a road type condition, or an average speed map condition.

11. The method of claim 10, wherein applying a set of bandwidth filters further comprises:
determining a noise frequency range for a noisy signal in the set of signals;
determining whether a minimum frequency of the noise frequency range exceeds a threshold frequency; and
applying a low-pass filter to the noisy signal when the minimum frequency exceeds the threshold frequency, wherein the low-pass filter has a cutoff frequency less than the minimum frequency.

12. The method of claim 11, wherein applying the set of bandwidth filters further comprises applying a band-stop filter to the noisy signal when a width of the noise frequency range is less than a threshold width, the band-stop filter attenuating the noisy signal within the noise frequency range in the frequency domain.

13. The method of claim 12, wherein determining the noise frequency range and width of the noise frequency range causes the change to the set of control variables, and wherein dynamically adjusting the set of bandwidth filters further comprises applying the low-pass filter or the band-stop filter to the noisy signal.

14. The method of claim 10, further comprising determining an event class associated with the event based on the set of filtered signals and a set of vehicle parameters reflecting physical characteristics of the vehicle, wherein the event threshold is based on the event class and a set of event factors based on the event class, and wherein determining the event class causes the change to the set of control variables.

15. The method of claim 14, wherein:
the set of signals is associated with a set of signal weights based on the control variables;
the event score is further based on the set of signal weights; and
dynamically adjusting the event score further comprises modifying the set of signals and the set of signal weights.

16. The method of claim 14, wherein:
the set of event factors is associated with a set of factor weights based on the control variables;
the event threshold is further based on the set of factor weights; and
dynamically adjusting the event threshold further comprises modifying the event class, the event factors, or the factor weights.

17. The method of claim 10, further comprising outputting event data when the event score exceeds the event threshold for the event and each of the subsequent events.

18. A tangible, non-transitory computer-readable medium storing instructions, that, when executed by at least one processor, cause the at least one processor to perform a method for dynamically controlling sensor-based data acquisition in vehicles, comprising:
receiving a set of signals associated with a set of sensors in a vehicle, wherein the set of signals is associated with a set of sampling rates;
applying a set of bandwidth filters to the set of signals to create a set of filtered signals; and
detecting an occurrence of an event by comparing an event score based on the set of filtered signals with an event threshold, wherein:
at least one of the set of signals, the set of sampling rates, the set of bandwidth filters, the event score, or the event threshold is dynamically adjusted based on a change to a set of control variables,
the set of control variables is changed in response to detecting occurrences of subsequent events, wherein each change to the set of control variables causes a modification to at least one of the set of signals, the set of sampling rates, the set of bandwidth filters, the event score, or the event threshold;
a set of local control variables based on the set of signals; and
a set of external control variables based on a hazard index received from the control system,
the event threshold is inversely proportional to the hazard index,
the hazard index is based on the event data and a set of boundary conditions reflecting conditions external to the vehicle, and
the set of boundary conditions includes at least two of a weather condition, a traffic condition, a road type condition, or an average speed map condition.

* * * * *